United States Patent [19]
Turner et al.

[11] Patent Number: 5,455,332
[45] Date of Patent: Oct. 3, 1995

[54] CARCINOMA-MARKING MONOCLONAL ANTIBODIES ELICITED WITH SYNTHETIC ASIALO-GM1 ANTIGEN

[75] Inventors: Connie J. Turner; Bryan M. Longenecker; David J. Willans, all of Edmonton; Antoine A. Noujaim, Sherwood Park; Grant MacLean, Edmonton, all of Canada

[73] Assignee: Biomira, Inc., Edmonton, Canada

[21] Appl. No.: 353,162

[22] Filed: May 12, 1989

Related U.S. Application Data

[63] Continuation of Ser. No. 927,277, Oct. 27, 1986, abandoned.
[51] Int. Cl.$^6$ .................... C07K 15/28; G01N 33/574
[52] U.S. Cl. ..................... 530/387.7; 530/388.8; 530/391.3; 435/7.23
[58] Field of Search .................. 435/172.2, 240.27, 435/7.23; 436/543, 548, 822, 823; 530/387, 389, 402, 807, 808, 391.3; 935/89, 93, 106

[56] References Cited

U.S. PATENT DOCUMENTS 4,798,719  1/1989  Ballou ..................... 424/1.1

FOREIGN PATENT DOCUMENTS 0211368  2/1987  European Pat. Off. .
2109407  6/1983  United Kingdom .

OTHER PUBLICATIONS

B. M. Longenecker, et al., Monoclonal Antibody Against a Cryptic, Etc., Int. J. Cancer: 33: 123–129 (1984).
Georg F. Springer, T and Tn, General Carcinoma Autoantigens, Science: 224: 1198–1206.
Georg F. Springer, et al., Breast Cancer Patient's Cell, Etc., Cancer 45: 2949–2954 (1980).
Irving L. Spar, An Immunologic Approach to Tumor Imaging, Seminars in Nuclear Medicine, 6: 4: 379–387 (Oct. 1976).
Rahman, et al., J. Immunol., vol. 129, No. 5, (1982), pp. 2021–2024.
Kohler, et al., Nature, vol. 256, (1975), pp. 495–497.
Hakomori, Monoclonal Antibodies Directed to Cell–Surface Carbohydrates in Monoclonal Antibodies and Functional Cell Lines 67–94 (Kennett, et al., eds. 1984).
Roitt et al., *Immunology*, The C. V. Mosby Company, St. Louis, 1985, pp. 8.2 and 8.3.
Hoppner et al., *Vox Sang.*, vol. 48, pp. 246–253 (1985).
Studen, I., et al. Glycoconjugate J., vol. 2 (3–4), pp. 303–314 (1985). Abstract only.

*Primary Examiner*—Toni R. Scheiner
*Attorney, Agent, or Firm*—Iver Cooper

[57] ABSTRACT

Monoclonal antibodies produced after immunization with a synthetic antigen bearing the structure Gal (beta 1-3) Gal-Nac beta-glycosidically linked to a carrier moiety are useful as carcinoma markers. Radioimmunoimaging agents are described in which such antibodies are tagged with radiometals or radiohalogens. Radiolabeled monoclonal antibody 155H.7, elicited by this antigen, rapidly localizes and persists in tumor tissues, demonstrating its utility as a tumor imaging agent.

5 Claims, 7 Drawing Sheets

| STRUCTURE OF TERMINAL DISACCHARIDE | NAME | TRIVIAL NAME |
|---|---|---|
|  | β-D-Gal-(1→3)-α GalNAc-O-R | T |
|  | β-D-Gal-(1→3)-β GalNAc-O-R | aGM₁ |

CARCINOMA-MARKING MONOCLONAL ANTIBODIES ELICITED WITH SYNTHETIC ASIALO-GM1 ANTIGEN

This application is a continuation of Ser. No. 06/927,277, filed Oct. 27, 1986, now abandoned.

BACKGROUND OF THE INVENTION

This invention relates to the use of a synthetic Asialo GM1 (T-beta) antigen to elicit production of monoclonal antibodies which bind to tumor cells.

T-alpha antigen, also known as the TF (Thomsen-Friedenreich) antigen, is the immediate precursor of the human blood group MN antigens. Tn, in turn, is the immediate precursor of the T-alpha antigens. Normally, T-alpha antigens are not accessible to the human immune system because they are masked by sialosyl groups. Friedenreich exposed the T-alpha antigen by treatment of red blood cells with neuraminidase, whereupon they were bound by anti-T components of human sera.

Kim and Ohlenbruck determined that the immunodominant portion of the T antigen was the disaccharide beta-D-Gal-(1-3)-alpha-D-GalNac. Z. Immun-Forsch. 130:88–89 (1966). It was later established that in contrast to healthy tissues, certain adenocarcinomas presented T-alpha and Tn determinants in reactive, unmasked form. Springer, et al., Cancer, 45:2949–54 (1980).

This T-alpha determinant has been prepared synthetically. Ratcliffe, et al., Carbohydr. Res., 93:35–41 (1981); Lemieux, EP Patent 44,188 (publ. May 28, 1986). Example 11 in the latter reference describes the use of T-alpha hapten on an HSA carrier (at incorporations of 7, 12, 14 and 22 haptens per HSA molecule) to detect a delayed type hypersensitivity response. The use of such haptens in the production of anti-T-alpha monoclonal antibodies was not mentioned. A synthetic T-alpha hapten is also described by Kolar, U.S. Pat. No. 4,442,284.

Rahman and Longenecker, J. Immunol., 129:2021–2024 (1982) used the natural form of the T-alpha antigen (neuraminidase-treated erythrocytes) for the production of monoclonal antibodies whose binding to these cells was competitively inhibited by synthetic T-alpha hapten. Thus, their use of synthetic T-alpha hapten was as a characterizing agent.

Asialo-GM1, a gangliotetraosyl ceramide with the structure Gal (beta 1-3) GalNac (beta 1-4) Gal (beta 1-4) Glc (beta 1-1) ceramide, is found in brain tissue in its sialated form. The immunodominant portion of this molecule (the terminal disaccharide), shown in boldface, differs from that of TF by the substitution of a beta linkage (underlined) for an alpha linkage, and hence is referred to herein as T-beta (as distinct from T-alpha). Lemieux, U.S. Pat. No. 4,137,401 discloses reaction conditions for linking a bridging arm to an aldose by a beta-D-anomeric glycosidic linkage. Synthetic T-beta haptens have been used in a number of immunological studies. Hoppner, et al., Vox-Sang., 48:246–53 (1985); Rahman and Longenecker, supra; Longenecker, et al., Int. J. Cancer, 33:123–129 (1984). However, use of synthetic T-beta haptens in production (as opposed to characterization) of monoclonal antibodies is novel.

Kasai purified the asialo GM1 glycosphingolipid and used it to prepare polyclonal anti-asialo GM1 antibodies. Eur. J. Immunol., 10:174–80 (1980).

The terminal disaccharide of asialo GM1 is of interest because it, like T-alpha, appears to be a tumor-associated antigen. Habu, et al., J. Immunol., 125:2284–88 (1980); Nakahara, et al., New Eng. J. Meal. 302:674–677 (1980). Hakomori tried and failed to make a monoclonal antibody to asialo GM1. Hakomori, in Monoclonal Antibodies and Functional Cell Lines: Progress and Applications, 67–100 (1984).

Goldenberg, U.S. Pat. No. 4,444,744 generically describes the use of radiolabeled antibodies to tumor cell surface antigens for diagnostic purposes. He teaches broadly that antibodies may be labeled by radiohalogen substitution or by chelation to a radiometal such as Indium-111. As one in a long litany of tumor cell surface antigens, he mentions T antigen. We have not seen any reports of radioimaging work on T-like structures in any of Dr. Goldenberg's work. Metal chelate-conjugated monoclonal antibodies are disclosed by Gansow, U.S. Pat. No. 4,454,106 and U.S. Pat. No. 4,572,509. On immunotherapy and immunoimaging see generally Monoclonal Antibodies: Potential Applications to the Treatment of Cancer, Seminars in Oncology, 13(2):165–179 (June, 1986).

Other references of interest are Irie, U.S. Pat. No. 4,557,931 and Adachi, U.S. Pat. No. 4,389,392.

SUMMARY OF THE INVENTION

We have used both synthetic T-alpha and synthetic T-beta (See FIG. 1) glycoconjugates to immunize mice for monoclonal antibody production. None of the antibodies which we generated using T-alpha reacted with human carcinomas. Surprisingly, many of the antibodies elicited by the T-beta immunogen reacted with many human lung, colon and breast carcinomas.

Our preferred T-beta immunogen is an HSA carrier molecule bearing the immunodominant disaccharide group at a concentration of 30–50 residues of asialo GM1 hapten per albumin molecule..

Our preferred monoclonal antibodies are 155H.7 and 170H.82. 155H.7 binds to T-beta when conjugated with HSA, but not to T-beta conjugated with BSA. Its differentiation of HSA and BSA may be advantageous in certain types of immunoassays.

Radiolabeled 155H.7 is an excellent tumor imaging agent. The antibody has been found to be retained by spontaneous tumors in dogs for as long as 30 days after injection. The antibody has also proven useful in imaging spontaneous tumors in man.

155H.7, with a suitable label, may also be used in immunohistopathology, particulary of carcinomas.

170H.82, suitable for serum assays for cancer.

Interestingly, all antibodies made against T-beta to date crossreact with T-alpha. As used herein, the term "animal" includes man.

DETAILED DESCRIPTION OF THE INVENTION

Preparation of Synthetic Haptens

There are several reported methods for the preparation of both T and asialo GM$_1$. Boniface, et al., in Current Applications in Radiopharmacology 157–64 (Pergamon Press: 1986); Ratcliffe, et al., Carbohydr. Res., 93:35-41 (1981).

The latter can then be conjugated to the HSA carrier via ozonolysis. Bernstein and Hall, Carbohydr. Res., 78:C1–C3 (1980).

Synthetic Antigens

The synthetic disaccharides which were used in our experiments, whether in the alpha or beta configuration, were conjugated to HSA with 30-50 carbohydrate residues per molecule of HSA. Estimation of the number of residues was performed using the phenol-sulfuric acid method. Dubois, et al., Anal. Chem., 28:350-66 (1956).

Monoclonal Antibody Production

BALB/c (RBF/Dn) were immunized according to a recently described protocol. Cianfriglia, et al., Hybridoma, 2:451-57 (1983); Taggart, et al., Science, 219:1228-30 (1983). The resulting clones were initially screened on the synthetic antigen used for immunization and the carrier protein HSA. Definitive tissue specificity testing was performed in one of our laboratories on normal and malignant human tissues from a large frozen tissue bank using avidin-biotin complex immunoperoxidase staining of frozen sections. We have also examined the tumor specificity of the generated antibodies to a number of neoplastic and normal carrier tissues.

Purification Of Monoclonal Antibodies

A number of methods have been proposed for the separation of a MAb from its ascites mixture. Depending on the isotype, protein concentration and the desired final elution concentration, one might select either an affinity-type, ion-exchange or a high performance liquid chromatographic system of separation. No method is ideal for all MAbs and some loss of immunoreactivity is expected as the procedure becomes more complicated.

The use of Protein A coupled to a solid support is a common method for the purification of IgG-type antibodies. Protein A, a bacterial lectin consisting of a single polypeptide chain with an approximate molecular weight of 42,000 daltons and usually isolated from a strain of S. aureus that does not incorporate the protein into its cell wall, has been shown to bind to the Fc portion of IgG molecules and very weakly, if at all, to IgA, IgM or IgE antibodies of many mammalian species.

Additionally, certain subclass separation has been achieved since Protein A will bind strongly to IgG of subclass 2a, 2b and 3 but weakly to subclass 1 of murine origin. IgGs of subclass I can be purified on Protein A with remarkable results by using a proprietary 'binding buffer' of unknown composition, available from Bio-Rad, see BioRad Bulletin #1172 . MAb-155H.7 was determined to be of the IgG-2b subclass using a commercial isotyping kit and therefore amenable to Protein A purification.

Figure 1:
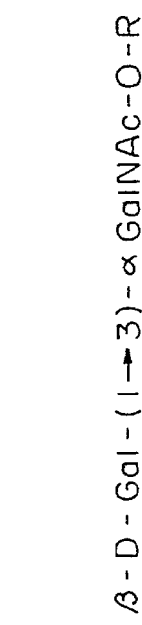
FIG. 1 shows the structure of the T and aGM$_1$ epitopes.
Figure 1:
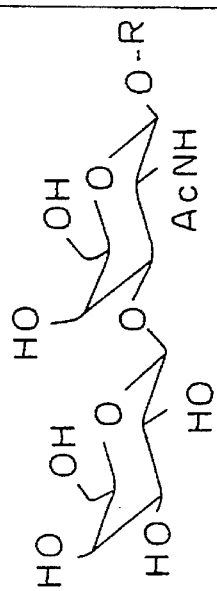
Figure 2A:
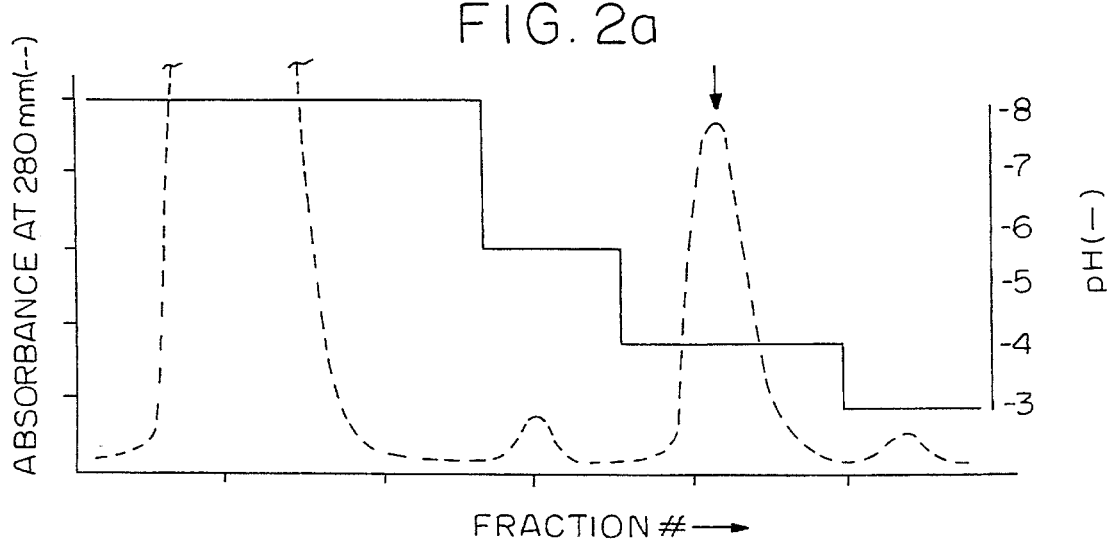
FIGS. 2a, 2b and 2c show elution profiles from the chromatographic purification of MAb-155H.7 ascites on (a) Protein-A-Sepharose, (b) DEAE-cellulose, and (c) HPLC hydroxylapatite. The ascites for (b) and (c) were first purified by ammonium sulfate precipitation. Arrows mark the MAb-155H.7 peaks.
Figure 2B:
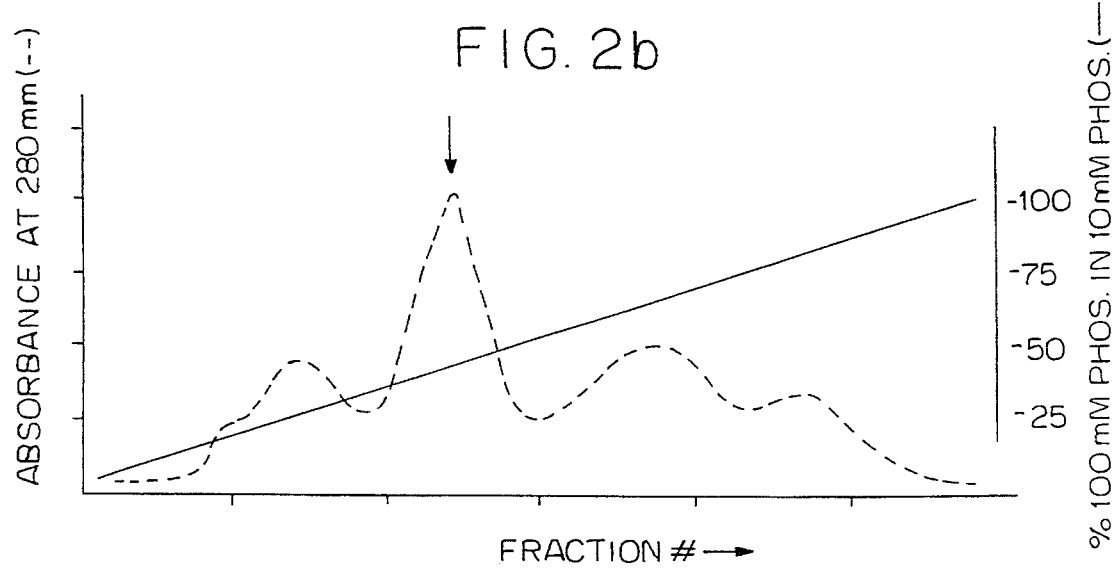
Figure 2C:
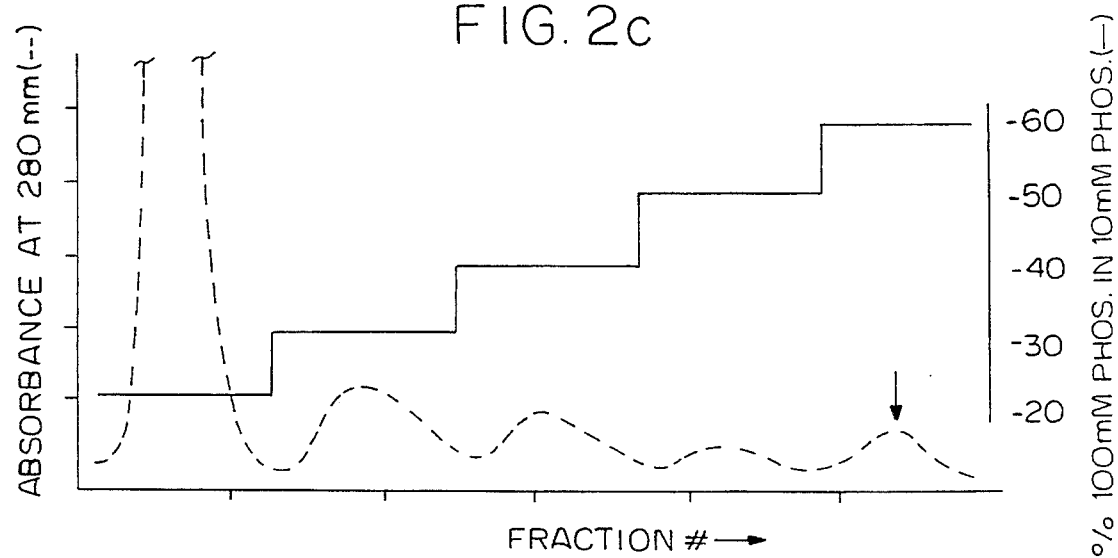

Other methods were also used successfully for the purification of MAb-155H.7, such as DEAE-cellulose and hydroxylapatite HPLC but Protein A proved to be the most efficient adsorbent. FIG. 2 illustrates the typical elution profiles for MAb155H.7 using these methods.

The ascites fluid was clarified by centrifugation prior to the separation to remove particulate matter and lipids. These materials, if left in the ascites preparation, will obstruct column flow and impede the elution process. The clarified ascites was then diluted I:1 with starting buffer (0.05M Tris, pH-8.5) or precipitated with ammonium sulfate. The latter procedure was employed when very large amounts of ascites required purification. Ammonium sulfate not only concentrates the protein of interest but also removes a large portion of the unwanted, nonspecific proteins such as albumin from the preparation. An ammonium sulphate concentration of 33% should precipitate essentially all the immunoglobulins and eliminate approximately 75% of the irrelevant proteins in the ascites fluid. The most soluble protein, albumin, only completely precipitates in the presence of 100% saturated ammonium sulfate. Initial screening of the supernatant and redissolved 33% ammonium sulphate precipitate indicated that a substantial amount (50%) of MAb-155H.7 remained unprecipitated. Therefore, a 50% ammonium sulphate precipitation followed by a 33% precipitation was adopted to produce high recoveries of the MAb of interest. Salting out of proteins in this manner is a mild form of precipitation and causes little protein denaturation. The major drawback is the time consuming dialysis needed to remove the large amounts of salt still remaining in the redissolved precipitate.

The elution of MAb-155H.7 from the Protein A column was accomplished using a step-wise gradient of 0.1M sodium titrate from pH=5.5 to 3.0. Each fraction collected was assayed for protein content and for immunoreactivity to T-beta by ELISA. ELISA of the ascites before and after purification indicated virtually no loss of immunoreactivity. Table 1 summarizes this immunoreactivity data which can be expressed in terms of the amount of antibody present in relation to the measured absorption units at 405 nm in the standard ELISA. The pg/A405 index adopted by our laboratory relates the absorbance reading at 405 nm to the amount of protein added to the ELISA. This index was found to be extremely useful in monitoring the specific immunoreactivity of our MAbs, particularly when comparative quantitation of MAb immunoreactivity was required, such as from aging clones or after radiolabeling.

TABLE 1

Table 1. Binding of MAb-155H.7 to Various T-beta Conjugates by ELISA.

| ELISA units | T-beta HSA (A*) | T-beta HSA (B*) | T-beta KLH | T-beta BSA | HSA |
|---|---|---|---|---|---|
| batch 1** | 82 | — | — | — | 270 |
| Batch 2** | 2024 | 16493 | 0.0 | 0.0 | 10390 |

*(1) Ascites from 0–3?month old clones;
(2) Ascites from 3–6 month?old clones
*A = 30–50 residues T-beta HSA and B is less than or equal to T-beta HSA
**Batch 1 represents MAb 155H.7 purified within three months after the ascites was produced.
Batch 2 represents MAb 155H.7 purified 3–6 months after ascites was produced.
All numbers represent the amount of purified MAb 155H.7 in pg required to give 1 absorbance unit at 405 nm in the standard ELISA with the specified conjugate.

As seen in Table 1, about 2 ng of MAb protein from a six month old clone were required to produce one absorbance unit whereas only 82 pg of the same protein fraction produced this absorbance when the clone was only a month old.

TABLE 2

Table 2. Analysis of Protein A Purified MAb-155H.7 From Mouse Ascites

| Protein A Elution pH | Ascites from 0–3 Month Old Clones[1] | | Ascites from 3–6 Month Old Clones[1] | |
|---|---|---|---|---|
| | pg/A$_{405}$ | mg/ml[3] Ascites | pg/A$_{405}$[2] | mg/ml[3] Ascites |
| 5.5 | 35324 | 0.25 | 31300 | 0.01 |
| 4.0 | 82 | 3.16 | 2024 | 0.49 |
| 3.0 | 206 | 0.06 | 1162 | 0.01 |

Note:
each value is the mean of 3–6 determinations
1. Clones stores in liquid nitrogen prior to ascites production
2. Index reflecting the quantity of MAb necessary to produce 1 absorbance unit in standardized ELISA
3. mg of total protein/ml of ascites for each peak Although the peak eluted at pH=3.0 contains similar immunoreactivity to that obtained at pH=4.0, the total amount of protein suggests that this is a small fraction of the active antibody that is retained by Protein A and only elutes at pH-3.0. Ey et al., Immunochemistry, 15:429 (1978) have suggested that IgG-1 antibodies elute between pH 5 and 6; IgG-2a, between pH 4 and 5; and IgG-2b, between pH 3 and 4. Since this antibody has been well characterized as an IgG-2b, it would appear not to follow this pattern. Stephenson et at., Anal. Biochem., 142:189 (1984), described the purification of a large number of murine monoclonals of IgG subclasses and showed that not one of the IgG-2b antibodies purified completely followed the scheme described by Ey. Although there seems to be a relationship to the pH used and antibody subclass, generalization is dangerous.

Characterization of Monoclonal Antibodies

Unlike the TF-alpha generated MAbs, several TF-beta generated MAbs showed moderate to strong reactivity with most human carcinomas. (Table 4)

TABLE 4

TUMOR REACTIVITY OF 155H.7 AND 170H.82

| | Pos | 155H.7 Heterogeneity | Pos | 170H.82 Heterogeneity |
|---|---|---|---|---|
| Lung | | | | |
| - Adenocarcinoma | 11/11 | 0/11 | 4/4 | 1/4 |
| - Squamous Carcinoma | 3/3 | 1/3 | 1/1 | 1/1 |
| - Undifferentiated Small Cell Carcinoma | 4/6 | 2/4 | 0/2 | — |
| - Poorly Differentiated Adenocarcinoma | 3/3 | 1/3 | 1/1 | 1/1 |
| - Poorly Differentiated Squamous Carcinoma | 3/3 | 1/3 | 2/2 | 2/2 |
| - Undifferentiated Large Cell Carcinoma | 6/9 | 1/6 | 1/2 | 1/1 |
| Total | 30/35 | 6/30 | 9/12 | 6/9 |
| Colon | | | | |
| - Colon Carcinomas | 24/24 | 1/24 | 12/12 | 5/12 |
| Total | 24/24 | 1/24 | 12/12 | 5/12 |
| Breast | | | | |
| - Infiltrating Lobular Carcinoma | 11/11 | 1/11 | 3/3 | 1/3 |
| - Infiltrating Ductal Carcinoma | 22/25 | 5/25 | 12/12 | 8/12 |
| - Medullary Carcinoma | 1/1 | 1/1 | 0/1 | — |
| - Mixed | 1/1 | 0/1 | — | — |
| Other Carcinomas | | | | |
| - Renal cell | 3/5 | 1/3 | 2/2 | 1/2 |
| - Gastric Carcinoma | 7/9 | 1/7 | 1/1 | 0/1 |
| - Prostatic Carcinoma | 2/2 | — | — | — |

These antibodies were relatively unreactive with normal cells (Table 5):

TABLE 5

REACTIVITY OF 155H.7 AND 170H.82 WITH NORMAL CELLS

| Tissue/Cell Type | 155H.7 | 170H.82 |
|---|---|---|
| Endocrine/Exocrine | | |
| Adrenal Cortical Cells (Zona Reticulis) | ++++ | − |
| Adrenal Medula | − | − |
| Thyroid | − | − |
| Hepatocytes | −/+ | − |
| Bile Ducts | ++ | ++ |
| Pancreatic Exocrine Tissue | + | + |
| Miscellaneous Glandular Epithelium (Skin adnexa etc.) | ++++ | ++++ |
| Breast Duct | ++++ | ++++ |
| Breast Lobules | − | − |
| Breast Lobule Cell (Involuting) | ++ | ++ |
| Nervous System | | |
| Parasympathetic Ganglia | ++ | ++++ |
| Parasympathetic Nerves | ++ | ++++ |
| Brain | − | +++ (Glial Cells) |
| Connective Tissue | −/+ | −/+ |
| Respiratory | | |
| - Glandular Epithelial Cells (Upper & Lower Airways) | ++++ | ++++ |
| - Normal Pneumocyte (Type I) | −/+ | + |
| - Reparative or Regenerative Pneumocytes (Type II) | ++ | ++ |
| - Exfoliated Mesothelial Cells (malignant effusions) | −/+ | −/+ |
| - Pulmonary Macrophages (near tumor site) | +++ | − |
| - Pulmonary Macrophages (non-proximal) | −/+ | — |
| Gastrointestinal | | |
| - Normal Glandular Epithelium (Small Bowel) | −/+ | −/+ |
| - Epithelium (Large Bowel) | −/+ | −/+ |
| - Squamous Epithelium (Esophagus) | − | − |
| Urogenital | | |
| - Renal Glomeruli | − | − |
| - Renal Tubular Epithelium (Normal) | −/+ | −/+ |
| - Renal Tubular Epithelium (Often tumour-bearing case) | +/++ | −/+ |
| - Prostatic Glandular Epithelium | +++ | +++ |
| - Uterine Glandular Epithelium | ++++ | ++++ |
| - Squamous Epithelium of Cervix | − | − |
| - Ovarian Follicular Epithelium | − | − |
| - Germinal Cells of Testis | − | − |
| - Normal Transitional Epithelium | −/+ | −/+ |
| Lymphoid & Hematopoietic tissue | | |

TABLE 5-continued

REACTIVITY OF
155H.7 AND 170H.82 WITH NORMAL CELLS

| Tissue/Cell Type | 155H.7 | 170H.82 |
|---|---|---|
| - Lymphoid tissues | – | – |
| - Spleen | – | – |
| - Bone Marrow | – | – |

IMMUNOPEROXIDASE STAINING TECHNIQUE FOR 155H.7+170H.82

1. Frozen sections cut at approximately 8 microns (kept in rack in cryostat at −20° C. until ready to stain).
2. PBS wash—5 min.
3. MAb preferably diluted at 1:500 (one drop normal horse serum to 10 ml dilution). Alternate dilutions 1:1000, 1:5000.
4. PBS wash—5 min.
5. Post-fix in 0.05% glutaraldehyde for 5 min. at 4° C. (sometimes this stage was deleted—i.e., no post fixation).
6. PBS wash—5 min.
7. Biotinylated Ab (1:200 dilution) 30 min.
8. PBS wash.
9. ABC colour rgt—60 min.
10. PBS wash.
11. Sigma DAB—66 µl of 30% $H_2O_2$ added to 10 ml DAB immediately prior to use.
12. PBS wash—5 min (alternatively tap $H_2O$ wash).
13. Hematoxylin (Harris, preferably, or Mayers) 2 min.
14. $H_2O$ wash—several changes.
15. 0.1% Acid Alcohol—35 sec.
16. $H_2O$ wash—several changes.
17. Saturated lithium carbonate—until sections turn blue.
18. $H_2O$ wash.
19. 3 Changes of Absolute Alcohol (10 dips each).
20. 2 Changes of Xylene (10 dips each).
21. Mount in permanent mounting media (non-aqueous).

Tissue Reactivity of Anti-Asialo-GM1 (T Beta) MAb 155H.7

The murine MAb 155H.7 was produced following immunization with synthetic TF-beta. It reacts strongly in ELISA with TF-alpha and TF-beta conjugated to HSA but shows little or no reactivity with Tn conjugated to HSA. It reacts with some normal tissues but reacts much more strongly with most cancers. Although hemopoietic tissues, hepatocytes, thymic epithelial tissues, connective tissues, most adrenal tissues and pancreatic acinar cells were negative, 155H.7 does react with the apical cytoplasm of some ductal glandular epithelial cells (in the gut, breast and bronchial tissues) with autonomic neurons, and it also reacts with the cytoplasmic glandular structures of adrenal cortical zones with reticularis and with trophoblastic cells of mature placentas. Although some malignant tissues are negative, those that are positive with 155H.7 characteristically react strongly than do corresponding normal tissues.

All normal lymph nodes tested as well as five lymphomas were negative for 155H.7. However, 155H.7 stained metastatic cancer cells in involved lymph nodes. Of 134 carcinomas tested, 119 (89%) were positive. 14% of the 119 showed marked or significant tumor heterogeneity (with negative and positive tumor cells) and another 6% showed minor or slight heterogeneity. Heterogeneity or negativity was more frequent in the central areas of tumors, whereas the cells in the growing or invading region of the cancers tended to be strongly positive.

In metastases the degree of homogeneity/heterogeneity with 155H.7 closely parallels the primary tumour, i.e., if the primary showed moderate heterogeneity then the metastases showed moderate heterogeneity. The most characteristic pattern observed was that both the primary and metastases carcinomas showed no evidence of heterogeneity.

As shown in Table 4, the common carcinomas tend to be positive. All colon carcinomas were positive. Of the five negative lung carcinomas, three were large cell undifferentiated and two were small cell undifferentiated cancers, while the four negative breast cancers were all poorly differentiated carcinomas. Accentuated membrane staining could be seen in certain preparations. 155H.7 was negative on 3/5 melanomas, 3/5 sarcomas, 2/5 renal cell cancers and 2/5 transitional uroepithelial cancers.

The in vitro binding of MAb 155H.7 to a variety of canine neoplasms is given in table 6. It is to be noted that the antibody in question bound surprisingly well to mesenchymal canine tumors, but not to canine serum albumin.

TABLE 6

155H.7 ABC Immunohistochemical Staining of Epithelial and Mesenchymal Canine Tumors

| Tumor type | Number of tumors 155H.7 Positive Number of tumors tested |
|---|---|
| A. Epithelial Tumors | |
| mammary adenocarcinoma | 6/12 |
| malignant mixed mammary tumor | 8/11 |
| benign mixed mammary tumor | 5/6 |
| mammary carcinosarcoma | 1/2 |
| mammary adenoma | 3/4 |
| lung carcinoma | 10/12 |
| perianal gland adenoma | 2/3 |
| perianal gland adenocarcinoma | 1/2 |
| squamous cell carcinoma | 1/7 |
| basal cell tumors | 0/3 |
| sebaceous gland adenocarcinoma | 1/1 |
| thyroid adenocarcinoma | 0/4 |
| transitional cell carcinoma | 0/1 |
| lacrimal gland adenocarcinoma | 0/1 |
| nasal adenocarcinoma | 0/1 |
| B. Mosenchymal Tumors | |
| osteogenic sarcoma | 8/8 |
| chondrosarcoma | 1/1 |
| fibrosarcoma | 2/2 |
| hemangiosarcoma | 3/3 |
| hemangioma | 1/1 |
| histio-sarcoma | 1/1 |
| histiocytoma | 2/3 |
| lymphosarcoma | 0/7 |
| hemangiopericytoma | 5/5 |
| rhabdomyosarcoma | 1/2 |
| leiomyoma | 4/4 |
| leiomyosarcoma | 0/1 |
| malignant melanoma | 2/2 |
| meningioma | 1/1 |
| mast cell tumor | 1/1 |

Similar to MAb 155H.7, 170H.82 appears to react more strongly with the tumor cells at the site of active invasion, or penetration or tumor growth.

Tissue Reactivity Of Anti-Asialo-GM1 (T-beta) MAb 170H.82

This MAb, seems very similar in tumor reactivity to 155H.7 except it demonstrates greater heterogeneity (See Table 4). However, 170H.82 does not react with parasympathetic or sympathetic neurons (in contrast to 155H.7), but it seems to react more strongly than 155H.7 on luminal cytoplasmic portions of bronchial epithelial cells. In addition, 170H.82 does not react with HSA.

Tissue Reactivities of Anti-TF-alpha MAbs

MAb 161H.4 which reacts specifically with T-alpha and not T-beta showed definite marking of a population of adrenal cortical cells, pulmonary macrophages, endocervical and $^{111}$In labeled MAbs gave us an insight as to the relative distribution of radioactivities in the mouse at various times after i.v. injection. $^{111}$In-B-EDTA-155H.7 cleared much faster than $^{131}$I-155H.7 from the blood. Liver uptake of $^{111}$In is elevated but is not as high as reported by others in the literature. The latter has consistently and expectedly shown increased levels in both liver and kidney. This is quite evident in the scintigrams observed at the various time intervals.

TABLE 7

TISSUE DISTRIBUTION OF MAb 155H.7 IN TA3/Ha TUMOR BEARING MICE[1]*

| TISSUE | 6 HR | | 24 HR | | 48 HR | | 72 HR | |
|---|---|---|---|---|---|---|---|---|
| | $^{131}$I-MAb | $^{111}$In-MAb | $^{131}$I-MAb | $^{111}$In-MAb | $^{131}$I-MAb | $^{111}$In-MAb | $^{131}$I-MAb | $^{111}$In-MAb |
| TUMOR | 8.85 ± 1.49 | 8.58 ± 0.60 | 7.34 ± 1.29 | 8.18 ± 0.64 | 4.83 ± 1.10 | 8.70 ± 1.40 | 3.95 ± 0.49 | 7.75 ± 0.59 |
| BLOOD | 25.33 ± 1.64 | 16.15 ± 0.78 | 11.42 ± 1.62 | 5.53 ± 0.61 | 7.30 ± 1.08 | 3.75 ± 0.29 | 9.82 ± 1.04 | 5.39 ± 0.32 |
| LIVER | 7.71 ± 0.88 | 6.10 ± 0.47 | 3.03 ± 0.50 | 5.93 ± 0.61 | 1.56 ± 0.28 | 5.76 ± 0.44 | 1.35 ± 0.12 | 5.70 ± 0.54 |
| SPLEEN | 4.00 ± 0.57 | 5.04 ± 0.34 | 1.96 ± 0.62 | 5.57 ± 0.47 | 0.47 ± 0.02 | 5.69 ± 0.47 | 0.53 ± 0.08 | 4.47 ± 0.27 |
| KIDNEY | 4.69 ± 1.14 | 18.25 ± 2.13 | 5.30 ± 0.25 | 21.37 ± 3.61 | 5.84 ± 0.55 | 19.08 ± 2.17 | 3.01 ± 0.83 | 13.12 ± 1.65 |
| MUSCLE | 0.81 ± 0.13 | 1.06 ± 0.15 | 0.54 ± 0.10 | 0.82 ± 0.08 | 0.38 ± 0.04 | 0.81 ± 0.04 | 0.34 ± 0.06 | 0.71 ± 0.02 |
| BONE | 1.28 ± 0.33 | 3.05 ± 0.56 | 1.50 ± 0.32 | 3.15 ± 0.39 | 0.31 ± 0.02 | 3.28 ± 0.38 | 0.23 ± 0.02 | 2.40 ± 0.39 |
| % OF ID REM** | 93.52 ± 8.53 | 87.46 ± 6.40 | 63.44 ± 14.66 | 79.53 ± 4.38 | 39.82 ± 5.47 | 76.04 ± 4.51 | 30.73 ± 0.67 | 63.76 ± 2.91 |

[1]PERCENT OF INJECTED DOSE/G OF TISSUE
*MEAN ± SD OF 5 MICE
**CALCULATED ON % DOSE PER ORGAN REMAINING IN THE ANIMALS epithelial cells and the cell surface of trophoblastic cells of the placenta. Despite this, MAb 161H.4 did not react with any of 8 breast carcinomas, 11 lung carcinomas, 4 colonic adenocarcinomas, 3 sarcomas, 1 poorly differentiated ovarian carcinoma, 1 renal cell carcinoma and a melanoma.

Another series of 31 MAbs specific for TF-alpha were tested against 2 colonic adenocarcinomas (both positive for 170H.82) and I pulmonary squamous carcinoma and were completely negative against these cancers. Three out of these 31 MAbs were arbitrarily chosen and further tested against 17 additional neoplasms and were found to be completely negative. Many of these TF-alpha MAbs, however, do react with neuraminidase treated human red blood cells (RBCs).

Biodistribution of MAb 155H.7

We have examined the cellular uptake of labeled MAb 155H.7 in a number of murine tumor cell lines maintained in our laboratory. These cells have been found in the past to concentrate radiogallium and some were also found to express T-like antigenic structures on their surface. Noujaim, et al., in Radioimmunoimaging and Radioimmunotherapy, 276–98 (Elsevier Press:1983). We have studied the differential uptake of these cells for 155H.7 which was labeled either directly with $^{125}$I or through a chelating agent (DTPA or benzyl EDTA) with $^{111}$In. However, no significant differences in uptake were noted between the radioiodinated antibody and its chelated form. That the TA3/Ha cell line shows a high concentration of the antibody is not surprising. We have previously demonstrated the preponderance of the T-like structure on this tumor both in vitro and in vivo. Shysh, et al., in Current Applications in Radiopharmacology, 248–55 (1986); Shysh, et al., Int. J. Cancer, 35:113 (1985). Consequently, we have examined the tissue biodistribution of labeled MAb 155H.7 in CAF$_1$ mice which were inoculated with Ta3Ha. Tumor tissue uptakes confirmed our previous observations on cellular concentration of the antibody (Table 7). The fact that we injected a mixture of $^{131}$I Artifacts during MAb Screening for Radioimmunoimaging Studies Specificity testing of MAbs frequently involves the use of frozen or fixed tissue sections as well as testing of cell lines. As a routine procedure in many laboratories the techniques involved in such studies entail the fixation of the test material with glutaraldehyde. The first evidence of the effect of the latter on the expression or detection of antigenic determinants on cell surfaces was seen when tissue sections were tested with MAbs under different conditions using immunoperoxidase.

It was clear that glutaraldehyde fixation modified the reaction of some MAbs with various cancers. Table 8 is representative of the aberration caused by glutaraldehyde fixation on the expression and detection of a series of differing antigenic determinants. MAb 50H.19 detects a cancer-associated glycoprotein and reacts strongly with most frozen sections of human adenocarcinomas yet very weakly with glutaraldehyde fixed cells. ELISA tests showed further that other MAbs also share this inconsistency of results. Whereas certain assumptions of negative reactions were often made, it became clear to us at a later period that certain MAbs were discarded simply on these erroneous conclusions. It thus appears that glutaraldehyde fixation may indeed reveal cryptic determinants that would not be accessible to a MAb when used in vivo. Conversely, treatment of tissues or cells with this reagent may sufficiently change the conformation of the surface antigen to make it unrecognizable by the immune system.

TABLE 8

Effect of Glutaraldehyde Fixation on MAb Immunoreactivity with Various Tumor Cell Lines as Tested by ELISA

| MAb[1] | Test Cell Line[2] | | | |
|---|---|---|---|---|
| | LoVo | | CAoV-3 | |
| | F[3] | NF[3] | F[3] | NF[3] |
| 50H.19 | 0.24 | 0.31 | 0.04 | 0.27 |
| 49H.8 | 0.58 | 0.11 | 0.08 | 0.20 |
| 166H.12 | 0.80 | 0.70 | 0.95 | 0.73 |
| 176H.7 | 0.25 | 0.69 | 0.11 | 0.32 |

1. MAb 50H.19 was generated against Mel-T. a human melanoma. 49-H.8 was generated against human neuraminidase-treated erythrocytes. 166H.12 was generated against a human small cell lung carcinoma which was kindly provided to one of us (GDM) by Dr. J. Minna. 176H.7 was generated against a drug-resistant subclone of the previous lung cell line, after treatment with cis-platin and vepesid (VP-16).
2. LoVo was kindly provided to one of us (GDM) by Dr. B. Drewinko. CAoV-3, an ovarian adenocarcinoma cell line, was obtained from the American Type Culture Collection.
3. F = fixed, NF = not fixed; ELISA absorbance measurements were conducted at 414 nm with 490 nm background subtraction. Measurements were made 20 minutes after substrate addition. Standard deviations were less than 10%.

The screening of hybridomas for the selection of useful MAbs for in vivo imaging should be conducted using multiple test systems prior to any conclusions being drawn.

Another artifact commonly encountered when testing the immunoreactivity of a particular MAb on a specific cell line is the result of cell recloning. Table 9 illustrates such effects. Since the MAbs are associated with cell-surface markers, any alteration in the fluidity or permeability of the membrane will invariably result in changes of marker distribution and concentration. As outlined in Table 9, continuous recloning of the same cell line resulted in a considerable increase in surface marker concentration, whether or not glutaraldehyde fixation was used.

TABLE 9

Effect of Recloning of Cell Line on Apparent Immunoreactivity

| MAb | Cell Line[1] | | | |
|---|---|---|---|---|
| | 209a R1 | | 209a R11 | |
| | F[2] | NF[2] | F[2] | NF[2] |
| 49H.8 | 0.15 | 0.14 | 0.26 | 0.29 |
| 50H.19 | 0.03 | 0.19 | 0.10 | 0.33 |

1. Results are shown for two sublines, R1 and R11 of a human small cell lung carcinoma (209a).
2. F = fixed, NF = not fixed; ELISA measurements were conducted at 414 nm with 490 nm background subtraction. Measurements made 20 minutes after substrate addition. Standard deviations were less than 10%.

Heterogeneity of Tumor Marker Distribution

Of great interest to histopathologists and yet of unfortunately little concern to many individuals engaged in immunoscintigraphic studies is the degree of heterogeneity in tumor-marker distribution within various tumors. Testing of the specificity of the MAbs was conducted through a number of cellular and histopathologic examinations. An illustrative example of tissue specificity and heterogeneity is given in Table 10. Two particular MAbs, 155H.7 and 170H.82, which showed great potential as candidates for further use in immunoscintigraphy, also showed considerable diversity of heterogeneity in histochemical staining.

TABLE 10

Immunoreactivity and Heterogeneity in Histochemical Staining of MAbs Generated Against the Same Cancer-Associated Marker

| MAb | No. of Carcinomas Tested | | % Positive | % Heterogeneity in Histochemical Staining |
|---|---|---|---|---|
| 155H.7 | 134 | beta-D-Gal (1–3) beta-D-GalNAc | 88.7 | 14.3 |
| 170H.82 | 52 | beta-D-Gal (1–3) beta-D-GalNAc | 88.5 | 45.7 |

Radioiodination of MAbs

Both Iodine monochloride (ICl) and Chloramine-T (Cl-T) are well known methods for introducing radioiodine into proteins. In the ICl method, radioactive iodide (*I$^-$) is equilibrated with ICl to produce *ICl with ICl carrier. The *I-Cl bond is slightly polarized such that *I possesses a partial positive charge at neutral pH. The major drawback is the addition of a certain amount of non-radioactive I from the ICl carrier into the protein reducing the specific radioactivity that can be obtained.

Cl-T is capable of producing no-carrier-added products. This compound is the sodium salt of the N-2 monochloro derivative of p-toluene sulfonamide and in aqueous solution at neutral pH actively oxidizes *I$^-$ to an electrophilic species, such as *IOH, which reacts primarily with the aromatic amino acids tyrosine and histidine, in an analogous fashion to *ICl. Although high specific radioactivity proteins can be produced by this method, proteins are more readily denatured by Cl-T than ICl.

To overcome the oxidative degradation induced by Cl-T and the relatively low specific radioactivity obtained with ICl, a recently introduced oxidizing agent, Iodogen (1,3,6,-tetrachloro-3-alpha,6-alpha-diphenylglycouril) has gained considerable attention. This commercially available compound is insoluble in aqueous media and reacts similarly to Cl-T to oxidize *I– to an electrophilic species. It is therefore capable of generating high specific radioactivity proteins with minimal oxidizing damage and requires no reducing agent to quench the reaction. E. Rogoeczi. Iodine-labeled Plasma Proteins vol. 1 CRC Press Inc., Boca Raton, Fla. (1984).

We have found that the best labeling yield was produced by Cl-T although this was only slightly higher than either ICl or the best Iodo-gen yield. The time needed to produce the best yield for both ICl (0.1 ug per 100 ug protein) and Cl-T (10 ug per 100 ug protein) was 30 seconds and is representative of the rapid incorporation of radioiodine produced by both of these reagents.

Iodo-gen, on the other hand, requires significantly more time to produce comparable yields due mainly to the fact that it is insoluble in the solution being iodinated. The yields were assessed by conventional gel filtration on BioGel P-6DG (BioRad) and were generally in the 30% range. Instances of erratic Iodo-gen yields were often related to the irreproducible mixing of the components from batch to batch.

Increasing the yield for ICl or Cl-T could be achieved with longer reaction times but this also increases the risk of protein damage as evidenced by decreased immunoreactivity of the MAb.

For routine radioiodinations, Iodo-gen was used in a ratio of 1 ug per 100 ug of MAb-155H.7 or 5 ug per 100 ug of a standard protein, polyclonal human IgG (poly-H-IgG).

Trichloroacetic acid (TCA) precipitation was used to analyze the radiochemical quality of, the purified radioiodinated proteins. It is based on the premise that only covalently bound radioiodine will precipitate with the protein. Greater than 98% was routinely associated with the TCA-protein precipitate from the void volume fraction of the gel column purification, indicating that a radioiodide-free preparation was obtained.

Preparation of Bifunctional Chelates

Monoclonal antibodies may alternatively be tagged by chelation with radiolabels. All glassware used in the synthesis of the bifunctional chelates, for the subsequent protein coupling reactions and for the radiometal attachment were washed in 50:50 nitric :sulfuric acid while buffers were either extracted with 0.01% dithizone or passed through a Chelex 100 (BioRad) column to remove extraneous metal ions. Water was double distilled and deionized to ensure high quality, cation-free solutions. The starting compound, p-nitrobenzylethylenediaminetetraacetic acid (PNB-EDTA) was synthesized in our laboratory using the method of Yeh et al., Anal. Biochem., 100:152 (1979). The p-aminobenzylethylenediaminetetraacetic acid (PABEDTA) was synthesized from PNB-EDTA as described by Leung, "The Covalent Attachment of 'Bifunctional Chelates' to Macromolecules and Their Use As Physical Probes in Biological Systems", Ph.D. Thesis (U. Cal./Davis, 1977). The p-bromoacetamidobenzylethylenediamine tetraacetic acid (BrAc-B-EDTA) was synthesized according to DeReimer et al., J. Med. Chem., 22:1019 (1979). All synthetic products were stored at −20° C. to maintain optimum chemical reactivity.

Bifunctional Chelate Labeling Procedure

Several aspects dealing with the use of BrAc-B-EDTA for radiolabeling proteins were investigated. Preliminary experience indicated the necessity of preparing the MAb in a concentrated alkaline solution possessing a high buffering capacity. Based on observations relating to protein solubility, protein concentration and buffer type, we eventually chose a 20 mg/ml protein level in a 0.2M phosphate buffer, pH=8.5. All subsequent BrAc-B-EDTA conjugation reactions were performed under these conditions.

The typical yields for the BrAc-B-EDTA reactions are given in Table 11.

sulfhydryl groups on proteins but can also react with free amino groups and other nucleophiles, Meenes and Feeney, Chemical Modification of Proteins, pp 68-138 San Francisco, Calif. (Holden-Day: 1971). This can be controlled to some extent with pH and when the chelate: protein ratio is kept low, sulfhydryl groups are the primary site of attachment. See Leung (1977) supra. These results suggest that MAb-155H.7 contains a higher free sulfhydryl content than poly-H-IgG. When the chelate ratio is increased, the difference is less notable although at 10:1 the percent yield is still higher for MAb-155H.7 than for the poly-H-IgG preparation.

The percent yield and available chelate ratio refer to the fact that the standard TLC and gel chromatography assay (based on the addition of a known amount of carrier indium) is only measuring chelates present on the protein that can bind $^{111}$In as opposed to the total chelate population attached to the protein. When the ratio is kept at 10:1 or less, the total available chelate present on the protein is less than 1:1 for both MAb-155H.7 and poly-H-IgG. This is in contrast to the work of Meares et al., Anal. Biochem 142:68 (1984) where an average ratio of 3:1 was obtained with a chelate: protein reaction ratio of 10:1. Only when the chelate: protein ratio is increased to 50:1 or 100:1 is there a significant increase in the total available chelate on the protein.

Using a chemical assay, Yeh, "New Bifunctional Chelates as Biophysical Probes II Diffusion Enhanced Lanthanide Energy Transfer Studies of Transferrin", Ph.D. Thesis (Univ. Cal/Davis, 1979) was able to determine the number of free sulfhydryl groups present on the HSA preparation he used for labeling studies with BrAc-B-EDTA. The total available chelate: protein ratio was calculated to be in a 3 fold excess to the number of sulfhydryl groups present. As well, at the end of reaction, no free sulfhydryl groups were detectable. This evidence suggests that the BrAc-B-EDTA first attacks the available sulfhydryl groups and then reacts with other nucleophiles present.

Labeling yields of no-carrier-added $^{111}$InCl$_3$ for the BrAc-B-EDTA labeled proteins ranged from 30% or less for proteins labeled at less than 1:1 available chelate: protein and greater than 95% for proteins containing 1:1 or more available chelates per protein molecule. This may indicate the unavoidable role of trace metal interference such that a

TABLE 11

REACTION YIELDS OF BrAc-B-EDTA CONJUGATION

| Available chelate per protein | BrAc-B-EDTA: Protein Reaction Ratio | | | | | | |
|---|---|---|---|---|---|---|---|
| | poly-H-IgG | | | | MAb-155H.7 | | |
| | 1:1 | 10:1 | 50:1 | 100:1 | 1:1 | 10:1 | 100:1 |
| 1) TLC$^1$ | ND$^3$ | 0.2 ± 0.02 | 5.5 ± 1.0 | 12.2 ± 3.1 | 0.2 ± 0.04 | 0.6 ± 0.06 | 7.2 ± 0.6 |
| 2) by GF$^2$ | ND$^3$ | 0.3 ± 0.0 | 5.3 ± 1.2 | 10.3 | — | — | — |
| 3) % labeling | ND$^3$ | 1.9 ± 0.1 | 10.0 ± 2.5 | 10.9 ± 1.7 | 21.4 ± 3.2 | 6.1 ± 0.6 | 7.2 ± 0.6 |

Note:
each value is the mean ± s.d. of 3 determinations
1. TLC = thin layer chromatographic assay
2. GF = gel filtration assay
3. ND = not detected It is interesting to compare the degree of conjugation for the two proteins observed under identical conditions. In the case of the 1:1 ratio, no detectable yield could be determined for poly-H-IgG whereas the best labeling yield of 21.4% was obtained for MAb-155H.7 for the same ratio. Haloacetamides of this type are known to react readily with free minimum background level of cation competition will always be observed in low chelate : protein preparations even at high concentrations. Purification of $^{111}$In labeled proteins was carried out using the mini-column procedure described later.

Contamination of Radiocation Preparations

The presence of non-radioactive metal contaminants in the radiocation solutions can also have a profound effect on the observed degree of radiolabel attachment to chelated proteins. From INAA (Instrumental Neutron Activation Analysis) experiments, it was determined that the significant amount of zinc present in the $^{67}GaCl_3$ preparation had deleterious effects on the chelation of $^{67}Ga$ to unconjugated chelate under acidic conditions. Turner, et al., In Current Applications in Radiopharmacology Determination of Metal Ion Impurities in Radiogallium Preparations and their Effects on the Radiolabeling of Chelated Proteins, M. W. Billinghurst ed. pp. 309–315 (Pergamon Press:1986). We have studied these effects using chelate labeled poly-H-IgG as a model protein with the radiometal in 0.1M citrate, pH 6.0. As shown in Table 12, there are significant problems in trying to chelate $^{67}Ga$ to the labeled protein. The amount of zinc already present in the undiluted stock solution is enough to prevent the chelation of $^{67}Ga$ to the labeled protein. This amount was estimated to be 5,000 to 12,000 times that of the $^{67}Ga$ on a molecular basis. It is not surprising then that the $^{67}Ga$ failed to bind to the B-EDTA-poly-H-IgG when relatively small amounts of chelated protein were used and that only 13% of the 67Ga could be chelated even at high concentrations. In comparison, $^{111}InCl_3$ solutions were readily chelated even at very low chelated protein concentrations indicating a relative lack of competing cations.

TABLE 12

Binding of $^{67}Ga$ and $^{111}In$ to Poly-H-IgG-B-EDTA[1]

| Amount of Chelate on Protein (nmoles) | % of Radioisotope Bound[2] | |
|---|---|---|
| | $^{67}Ga$ | $^{111}In$ |
| 0.066 | 0 | 92 |
| 0.663 | 4.1 | 93 |
| 6.63 | 6.6 | 98 |
| 66.3 | 8.9 | 98 |
| 663 | 13.3 | 98 |

1. From C. J. Turner, et al., in 'Current Applications in Radiopharmacology', M. W. Billinghurst, ed., Pergamon Press, Toronto, 1986.
2. Using 1 ul of stock radioisotope solution Radiochelate Stability The stability of the radiometal chelated protein in solution is important when determining the shelf life to the labeled product. Table 13 summarizes the results of an extended stability study using chelate labeled poly-H-IgG. Baseline parameters indicated that virtually 100% of the $^{111}In$ is chelated to the protein. Only marginal losses of $^{111}In$ are apparent throughout the course of the study. The high stability of the 111In label in solution would allow preparation of the radio-chelated protein for subsequent use without the necessity of repurification.

TABLE 13

In Vitro Stability of $^{111}In$-B-EDTA-poly-H-IgG in 0.1 M Citrate Solution

| Time in hours | Percent Bound to B-EDTA-poly-H-IgG after incubation at | | |
|---|---|---|---|
| | 37° C. | 25° C. | 4° C. |
| 18 | 98.7 | 98.9 | 98.1 |
| 42 | 97.4 | 98.0 | 96.4 |
| 94 | 97.4 | 97.9 | 96.6 |
| 138 | 97.4 | 97.6 | 96.6 |

TABLE 13-continued

In Vitro Stability of $^{111}In$-B-EDTA-poly-H-IgG in 0.1 M Citrate Solution

| Time in hours | Percent Bound to B-EDTA-poly-H-IgG after incubation at | | |
|---|---|---|---|
| | 37° C. | 25° C. | 4° C. |

Note:
each value is the mean of 3 determinations

The stability of $^{111}In$-PAB-EDTA at its expected plasma level and in the presence of physiological concentrations of apotransferrin and HSA was tested over a 72 hour period. 111In, when injected IV as 111In-chloride, is known to bind very rapidly to transferrin. It is important therefore to determine the stability of the chelate complex in the presence of apotransferrin if the chelate is going to be used for in vivo applications such as immunoscintigraphy. The results of this stability study are presented in Table 14 and indicate that the chelate complex retains virtually all of its $^{111}In$ in the presence of apotransferrin. $^{111}In$-citrate was tested with albumin as a non-specific control and with apotransferrin as a positive control. These results suggest $^{111}In$ radioactivity detected in vivo will indeed represent the biodistribution of the radiochelate labeled MAb, at least until proteolysis or other metabolic degradation takes place.

TABLE 14

In Vitro Stability of $^{111}In$-PAB-EDTA in the Presence of Apotransferrin and HSA

| Complex/Protein | Percent of the Radioactivity Retained on the Complex after Incubation at 37~C with the Protein for the Following Items | | |
|---|---|---|---|
| | 24 hr | 48 hr | 72 hr |
| $^{111}In$-PAB-EDTA/Tf | 99.6 | 99.7 | 99.6 |
| $^{111}In$-PAB-EDTA/HSA | — | 97.1 | 96.4 |
| $^{111}In$-citrate/Tf | 0.30 | 0.27 | 0.32 |
| $^{111}In$-citrate/HSA | 98.8 | — | 99.7 |

Note:
each value is the mean of 3 determinations

Separation of Free Radiolabel

The separation of labeled protein from unreacted chelate, unreacted radiometal or radioiodide using gel exclusion chromatography is based on molecular weight size differences. We have compared conventional gel filtration with a centrifuged mini-column gel filtration technique. The conventional method is relatively simple and produces high yields of recovered protein with high reproducibility. The major drawback is the time required to complete the separation with a typical fractionation run being anywhere from 1 hour to several days. The desalting gels are considerably faster due to their structure and separations on these gels can be completed in as little as 30 minutes. However, there almost always is considerable sample dilution. For radiolabeled proteins this could be a major problem if subsequent use requires a high specific radioactivity based on sample volume, such as biodistribution and cell uptake studies. As well, accessory equipment such as UV flow monitors and fraction collectors for monitoring column eluate are often necessary and expensive. Many of these concerns can be eliminated or vastly simplified if the centrifuged mini-column technique is employed. This technique is also simple, produces good protein recoveries and is highly reproducible. The major advantages are the saving in time as it reduces a separation run to less than 15 minutes and the recovered sample is highly concentrated. Accessory equipment is usually limited to a table top centrifuge and the mini-column apparatus can be readily manufactured from available laboratory equipment.

We have found the best conditions for maximum protein recovery utilize a BioRad P-100 column (0.8×5.0 cm) centrifuged at 100× g for two minutes with one or two subsequent washes (100 ul) and recentrifugation. Our recovery of 80–85% is somewhat lower than that reported by Penefsky, Meth. Enzymol., 56:527 (1979) (98 to 100%) for a similar centrifuged column system using Sephadex G-50 as the gel material but correlates to that reported by Saul and Don, Anal. Biochem., 138:451 (1984) and Meares et al., Anal. Biochem 142:68 (1984) for similar centrifuged mini-column systems using Sephadex G-25 (Pharmacia) and Sephadex G-50-80 (Sigma) respectively. The addition of a 100 ul wash after the initial centrifugation improved protein recovery in all cases. When no wash buffer was added, protein was lost in the fluid trapped in the gel beads. With the addition of buffer, the gel is rehydrated and this protein can be recovered. According to Penefsky (1979), after the initial pre-centrifugation before sample addition, the gel beads are dehydrated considerably especially in the top one-third of the column. With addition of the protein sample, the gel absorbs the buffer in the sample along with most unbound ions and causes the protein to dehydrate. The protein can then be recovered in a highly concentrated form in a volume of buffer that is held within the lower portion of the column. Although breakthrough of unwanted compounds is less when no wash is applied to the column, the protein recovery is considerably reduced. Chelate, radiometal and radioiodide breakthrough were all less than 1.5% and this small amount could be attributed to non-specific adsorption to the protein used. When these columns were tested in the absence of protein, chelate, radiometal and radioiodide breakthrough was consistently less than 0.5%.

Evaluation of MAb Biological Integrity After Radiolabeling

The effects of radioiodination and the chelate reactions were tested by ELISA to determine how these procedures influenced the binding of the labeled MAb to the appropriate antigen. Although we have utilized a standardized ELISA to quantitate these effects, this indirect technique should be equally sensitive to all forms of MAb modification and therefore alterations in secondary antibody binding may also take place.

MAb-155H.7 has proven to be very sensitive to all three radioiodination methods but especially to ICl and Cl-T. These conclusions are based on the data presented in Table 15. Thirty second exposure to either one of these reagents reduces immunoreactivity by 80%. Iodo-gen induced alterations were more easily controlled by manipulating the exposure time and amounts of the reagent. The optimal reaction time and amount was 5 minutes of exposure to 1 ug of Iodo-gen. When $^{131}$I was used for radioiodinating MAb-155H.7, it was found that the percent immunoreactivity retained declined even faster with time. This is likely related to radiation induced damage generated by the beta component of $^{131}$I. Thus, not only the type of radioiodination reagent and the reaction conditions but also the radioiodine isotope itself can influence the final MAb quality.

TABLE 15

Percent of MAb-155H.7 Immunoreactivity Retained after Radioiodination Procedures

| Amount of Iodo-gen | Iodo-gen Reaction Time | | | ICl Reaction Time | CL-T Reaction Time |
|---|---|---|---|---|---|
| | 5 min. | 10 min. | 30 min. | 30 sec. | 30 sec. |
| 1 ug | 61.3 | 36.4 | 40.4 | 20.0 | 18.4 |
| 3 ug | 41.6 | 22.7 | 28.3 | — | — |
| 5 ug | 24.2 | 24.5 | 4.8 | — | — |

Note:
each value is the mean of 3 determinations

The effects of the BrAc-B-EDTA chelate reaction conditions on MAb-155H.7 immunoreactivity are summarized in Table 16. The control data for these studies was MAb-155H.7, at the same concentration as for the 10:1 and 100:1 chelate reactions, but without addition of the chelate reagent. This was to test the reaction conditions for effect on the MAb in the absence of the chelating agent. These results indicate that the MAb is sensitive to the reaction conditions employed and loses approximately 20% of its immunoreactivity at 15–120 minutes. The reaction conditions explored by Leung (1977) showed that no conjugation occurred at 4° C. and both Leung (1977) and Yeh (1979) favored elevated temperatures for the BrAc-B-EDTA reaction. When the chelating agent is present a further 20 to 25% reduction of immunoreactivity is observed after a 60 minute reaction time, with the maximum reduction being 30 to 35% after 2 hours. The net reduction of immunoreactivity is 44% for the 10:1 reaction and 48% for the 100:1 reaction. Thus, the reaction conditions and the presence of chelating agent conjugated to MAb-155H.7 have a definitive influence on its selective ability to interact with its specific antigen.

TABLE 16

Percent of MAb-155H.7 Immunoreactivity Retained after BrAc-B-EDTA Reaction Procedures

| Rxn. Time (minutes) | Stock MAb-155H.7 % of stock | Control[1] MAb-155H.7 % of stock | 10:1 Chelate: MAb % of stock | 100:1 Chelate:MAb % of stock |
|---|---|---|---|---|
| 0 | 100 | — | — | — |
| 15 | — | 85.9 | 84.1 | 76.8 |
| 30 | — | 83.3 | 85.9 | 64.0 |
| 60 | — | 82.8 | 58.7 | 52.3 |
| 120 | — | 78.3 | 44.2 | 47.8 |

Note:
each value is the mean of 4–9 determinations
1. Control MAb-155H.7 was incubated without chelating agent for 15–120 minutes under identical reaction conditions.

The major advantage of the chelation reaction over the radioiodination reaction is the preparation of the chelate-protein complex in advance of the actual radiometal labeling. In this way, a stock solution of the MAb can be labeled with the chelate and stored at −80° C. until needed. Under optimal conditions, all of the subsequently added radiometal becomes bound to the MAb via the chelate moiety, such that separation of free radioactivity need not be accomplished, and thus greatly simplifying final preparation. However, in practice, we have found that the removal of some free radiometal is usually necessary. The second distinct advantage is the availability of several radioisotopes for radiolabeling which possess more suitable physical decay properties, viz. $^{67}$Ga, $^{111}$In and others.

For routine $^{111}$In labelling, MAb 155H.7 conjugated with 0.6 chelate/molecule in 0.1M citrate buffer, pH 6.0 was mixed either directly with the required amount of $^{111}$InCl$_3$ or a solution of $^{111}$InCl$_3$ in 0.1M citrate, pH 6.0. After a 15 minute room temperature incubation, the labelled protein was tested by TLC to determine the labelling yield and if free $^{111}$In was to be removed. This procedure was accomplished by the mini-column technique described previously. Generally, yields of labelled product obtained ranged from 70-90%.

Binding of Radiolabeled Antibody to Tumor Surface Antigens (In Vitro)

Figure 3:
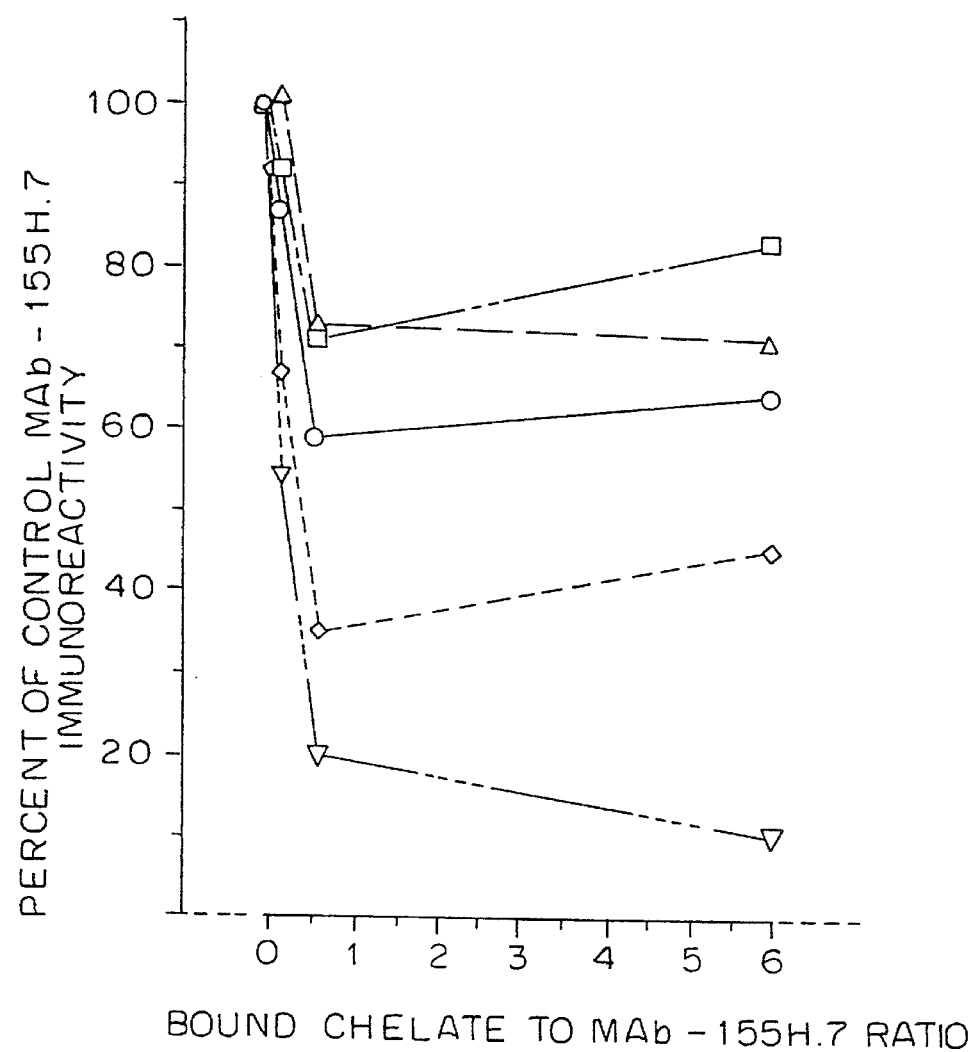
FIG. 3 shows the comparative immunoreactivity of chelate labeled MAb-155H.7 measured by tumor cell ELISA.

Two types of cellular assays, the whole cell ELISA and live cell uptake, were used for further in vitro characterization of the radiolabeled proteins. In the whole cell ELISA, used only for MAb-155H.7, murine and human tumor cell lines were grown in 96 well micro-liter plates and fixed using glutaraldehyde. The rest of the ELISA procedure was carried out comparing unlabeled MAb-155H.7 to the various radiolabeled forms of MAb-155H.7. FIG. 3 graphically demonstrates the results obtained, expressed in terms of unlabeled MAb binding. All cell lines tested showed some association of MAb-155H.7 in the unlabeled and radiochelate labeled forms. The effect of increasing amounts of chelate on the MAb is clearly seen by a decrease in association of the MAb with the cells. This is particularly true for the human cell lines, LoVo and SW1116. The other human cell line, MIA-PACA, as well as the murine cell lines, EMT-6 and RI, show moderate decreases with increasing chelate conjugation ratios. Similar tests have yet to be done to determine results without glutaraldehyde fixation.

Figure 4:
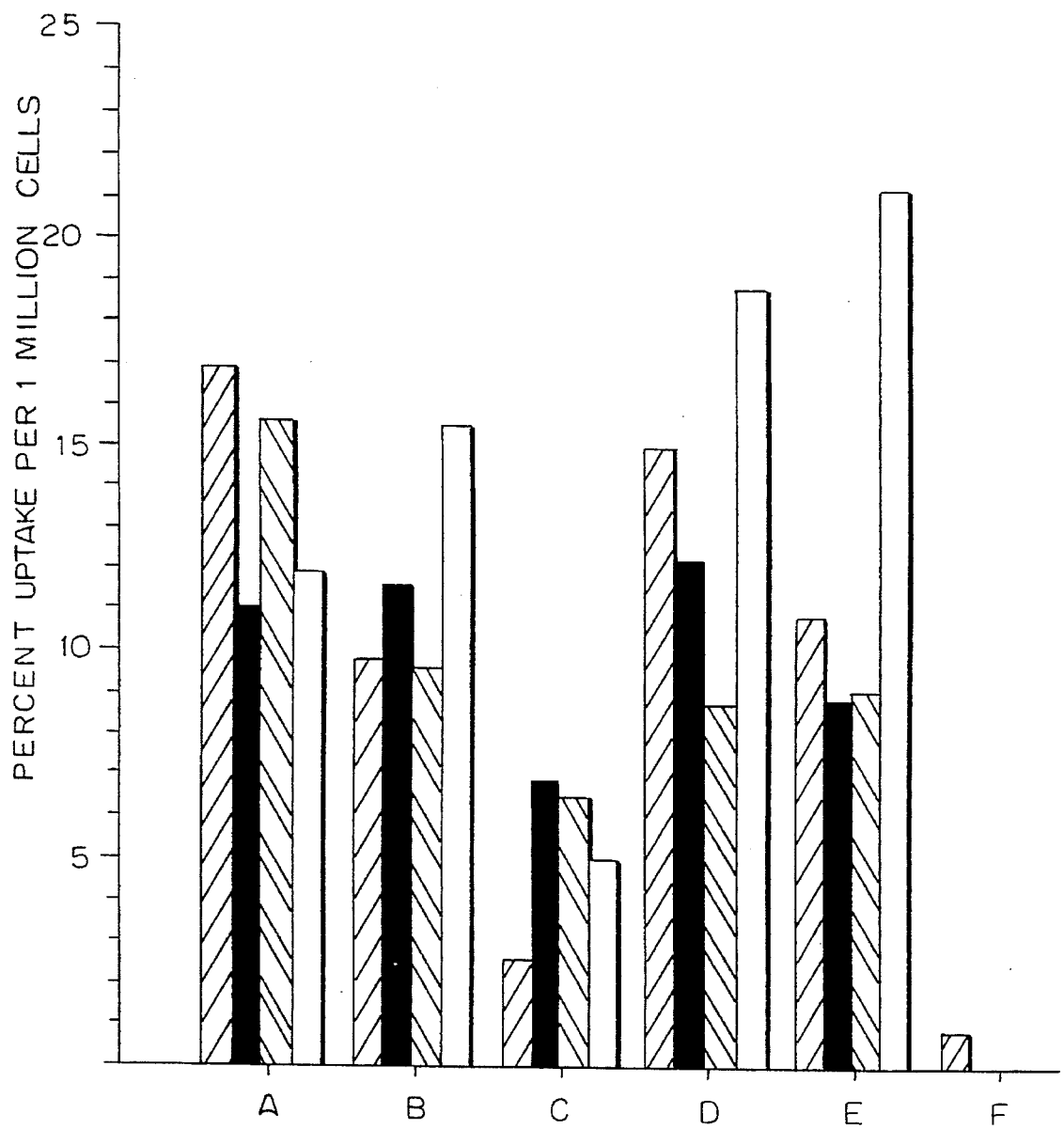
FIG. 4 shows comparative uptake of radiolabeled MAb- 155H.7 in murine tumor cell lines. The groups shown are (a) chelate $^{111}$In labeled MAb 0.6:), (b) chelate $^{111}$In labeled MAb (0:6:1) (c) $^{111}$In citrate, (d) $^{125}$I MAb 155H.7, (e) $^{125}$I poly-H-IgG, and (f) Na$^{125}$I.

FIG. 4 represents the percent uptake of each radiolabeled protein per 10$^6$ cells with $^{111}$In-citrate and Na$^{125}$I as radiolabel controls. The cells were suspended in serumless media (RPMI 1640) after being washed 3 times with the same solution. The radiolabeled proteins were diluted in PBS without the addition of 1% BSA.

From these results, a general trend of decreasing uptake with increasing amount of chelate on MAb-155H.7 is evident for EMT-6 and EL4 cells. For RI and TA3/Ha cells, the uptake remains the same or increases slightly for increasing chelate labeled to MAb-155H.7. In all cases, the uptake of$^{111}$In-B-EDTA-MAb-111H.7 is greater than $^{111}$In-citrate. Radioiodinated MAb-155It.7 shows similar or slightly better uptake when compared to $^{111}$In-labeled benzyl-EDTA-MAb-155H.7 ($^{111}$In-B-EDTA-MAb-155H.7) with uptake of Na$^{125}$I by all cell lines negligible.

The uptake of poly-Human-IgG (poly-H-IgG) is somewhat surprising since this is a non-specific immunoglobulin preparation and in some cell lines, such as TA3/Ha, is almost identical to that of the labeled MAb. The whole cell ELISA and standard ELISA with T-beta-HSA showed no binding of poly-H-IgG relative to MAb-155H.H7. This would suggest that the binding observed on these cell lines is either of nonspecific nature, since the uptake was performed in the absence of other proteins (FBS or BSA), or that the poly-H-IgG contained significant amounts of anti-T antibodies (specifically, anti-Tn and anti-T-alpha, since the assay against T-beta was negative). Springer, Science Vol. 224 June 1984 pp. 1198-1206, indicates that between 2.5 and 6 percent of human IgG is anti-T.

Another possibility is the presence of immunoglobulins of undefined origin in the poly-H-IgG preparation that are binding to other receptors on the cell surface and are therefore taken up to the same extent as the radiolabeled MAbs.

We have also studied the effect of the presence or absence of BSA and FBS in the preparations used for the cell uptake using the TA3/Ha tumor cells. These results are presented in Table 17 for the radioiodinated MAb-155H.7 and radiochelate labeled MAb-155H.7 with 6 chelates per protein molecule. The presence of both BSA and FBS severely inhibits the binding of MAb-155H.7 to TA3/Ha cells. When one or the other is present the inhibition is less than when both are present but still represents a significant reduction in the binding of the radiolabeled MAbs. BSA and FBS do not cross-react with MAb-155H.7 so the inhibition of binding must be through another mechanism or could be just due to the fact that these labeled proteins are associating nonspecifically to the cells in the absence of BSA or FBS. This nonspecific association could be blocked by the presence of BSA or FBS.

TABLE 17

Uptake of Radiolabeled MAb-155H.7 in TA3/Ha Cells in the Presence and Absence of FBS and BSA[1]

| Cells Incubated in: | MAb-155H.7 Diluted in: | | | |
|---|---|---|---|---|
| | PBS | | 1% BSA/PBS | |
| | $^{111}$In-MAb | $^{125}$I-MAb | $^{111}$In-MAb | $^{125}$I-MAb |
| PBS | 9.1 ± 1.1 | 12.6 ± 1.4 | 2.5 ± 0.2 | 0.8 ± 0.06 |
| PBS + 10% FBS | 1.6 ± 0.1 | 2.9 ± 0.8 | 0.4 ± 0.1 | 0.5 ± 0.06 |
| RPMI | 7.4 ± 1.0 | 12.6 ± 0.4 | 0.9 ± 0.06 | 1.0 ± 0.2 |
| RPMI + 10% FBS | 1.3 ± 0.08 | 2.0 ± 0.4 | 0.3 ± 0.06 | 0.3 ± 0.06 |

1. Each value is the mean ± s.d. of 3 determinations for the percent uptake per 10$^6$ cells in one hour at 37° C.

Binding of Radiolabeled Antibody to Synthetic Immunosorbent

Along with the testing in vitro cell systems, a radioactive binding assay (RBA) using T-beta-HSA and T-Synsorb (S) (ChemBioMed) was used to evaluate the antibody with a standard ELISA being conducted in parallel for comparison purposes. All incubations were performed for one hour at room temperature. Results for these assays are presented in Table 18.

TABLE 18

RBA and ELISA Data for Radioiodinated and Radiochelate-labeled MAb-155H.7 and Radioiodinated Poly-H-IgG on Various Forms of the T-antigen

| Protein | ELISA % of MAb-155H.7 | RBA on T-HAS | | RBA on T-beta -S[1] | | RBA on T-alpha -S[1] | |
|---|---|---|---|---|---|---|---|
| | | % Bound | ng bound | ng MAb/ nmole T | ng MAb/ mg T -S | ng MAb/ nmole T | ng MAb/ mg T -S |
| MAb-155H.7[1] | 100.0 | — | — | — | — | — | — |
| $^{111}$In-MAb- | 97.5 | 3.1 | 0.5 | 0.2 | 0.1 | 0.6 | 0.2 |

TABLE 18-continued

RBA and ELISA Data for Radioiodinated and Radiochelate-labeled MAb-155H.7 and
Radioiodinated Poly-H-IgG on Various Forms of the T-antigen

| | ELISA | RBA on T-HAS | | RBA on T-beta -S[1] | | RBA on T-alpha -S[1] | |
|---|---|---|---|---|---|---|---|
| | % of | | | ng MAb/ | ng MAb/ | ng MAb/ | ng MAb/ |
| Protein | MAb-155H.7 | % Bound | ng bound | nmole T | mg T -S | nmole T | mg T -S |
| 155H.7 (0.6:1)[4] | | | | | | | |
| $^{111}$In-MAb-155H.7 (6:1)[4] | 81.0 | 2.2 | 0.4 | 0.2 | 0.1 | 0.1 | 0.0 |
| $^{125}$I-MAb-155H.7 | 23.9 | 3.8 | 0.6 | 0.5 | 0.3 | 3.3 | 0.9 |
| $^{125}$I-Poly-H-IgG | 1.3 | 0.0 | 0.0 | 0.0 | 0.0 | 0.0 | 0.0 |

1. MAb-155H.7 = Unlabeled MAb-155H.7.?
2. T beta-Synsorb - 0.58 umoles per g of Synsorb, 1 mg = 0.58 nmoles (Chembiomed).
3. T alpha-Synsorb - 0.27 umoles per g of Synsorb, 1 mg = 0.27 nmoles (Chembiomed).
4. Available chelate: MAb-155H.7.

Although the radiochelate labeled MAb-155H.7 retained practically 100% of its binding to T-beta-HSA by ELISA as compared to only 24% for the radioiodinated MAb-155H.7, the percent bound by RBA was equivalent for all three proteins. The percent bound reported here has been corrected for any nonspecific binding of $^{111}$In-citrate and Na$^{125}$I in the absence of protein. As well, the poly-H-IgG shows no binding to T-beta-HSA in either the RBA or the ELISA which is another indication that there are no anti-T antibodies in this preparation.

The results obtained with T-beta-S and T-alpha-S represent binding of MAb-155H.7 to a commercial source of the synthetic T-antigen. Again, no correlation to the type of radiolabel can be seen in the binding to T-beta-S. The radioiodinated preparation of MAb-155H.7 shows higher binding to T-beta-S than to the T-beta-HSA used in the standard ELISA. The radiochelated preparation of MAb-155H.7 shows significantly reduced binding to T-beta-S when compared to the radioiodinated preparation which is opposite to the result obtained with the standard ELISA. Some correlation for the radiochelate labeled MAb-155H.7 can be seen in the binding to T-beta-S where the higher chelate substituted MAb-155H.7 shows reduced binding. However, the radioiodinated preparation shows a 7 fold increase in binding to T-alpha-S than to T-beta-S and is significantly higher in binding to T-alpha-S than the radiochelated MAb-155h.7. The difference observed in the binding indicates that the T-beta-HSA antigen is different from the commercially available T-Synsorbs and in this case the MAb-155H.7 binds better to the T-alpha-S than to the T-beta-S.

The various results presented here for the in vitro assays of MAb-155H.7 suggest that there is very little correlation between all the techniques used for quality control of the antigen binding activity of the MAb. Testing by RBA on T-beta-HSA and histology showed no difference whereas testing by RBA on the commercial T-Synsorbs showed higher binding for iodinated MAb-155H.7 over chelated labeled MAb when the iodinated preparation had lower in vitro binding than chelated MAb by standard ELISA. For this particular MAb, the standard ELISA on the antigen used for immunization appears to give the best indication of the effects of the radiolabeling techniques on the ability of the MAb to bind to its antigen.

DISTRIBUTION OF RADIOLABELED
MAb-155H.7 IN TUMOR BEARING MICE

Figure 5A:
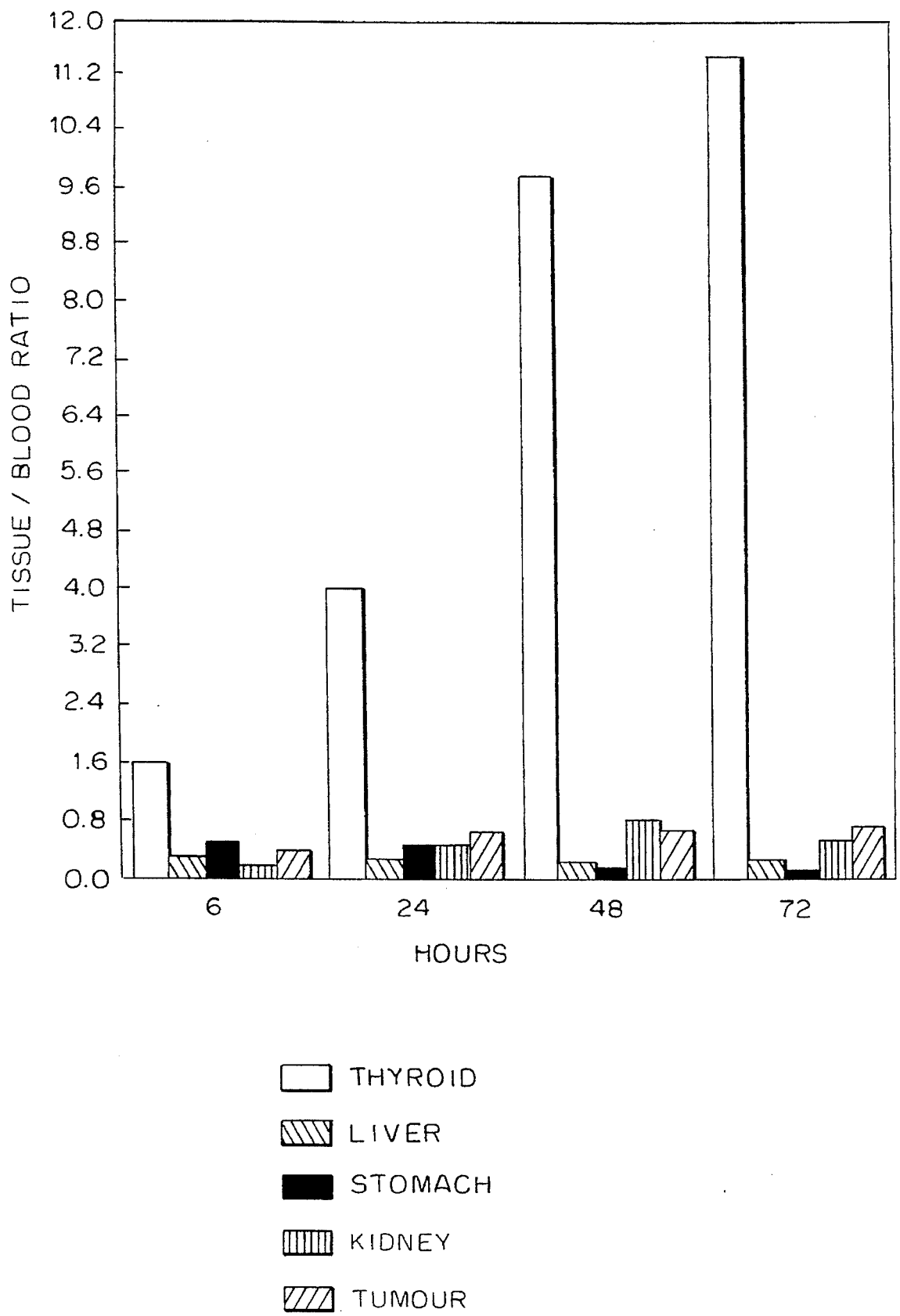
FIGS. 5A, 5B and 5C show tissue-to-blood ratios of (a) $^{131}$I-MAb-155H.7, (b) $^{111}$In-B-EDTA-MAb-155H.7 and (c) $^{125}$I-poly-H-IgG for various organs at 6, 24, 48 and 72 hours after injection into TA3/Ha-tumor bearing mice.
Figure 5B:
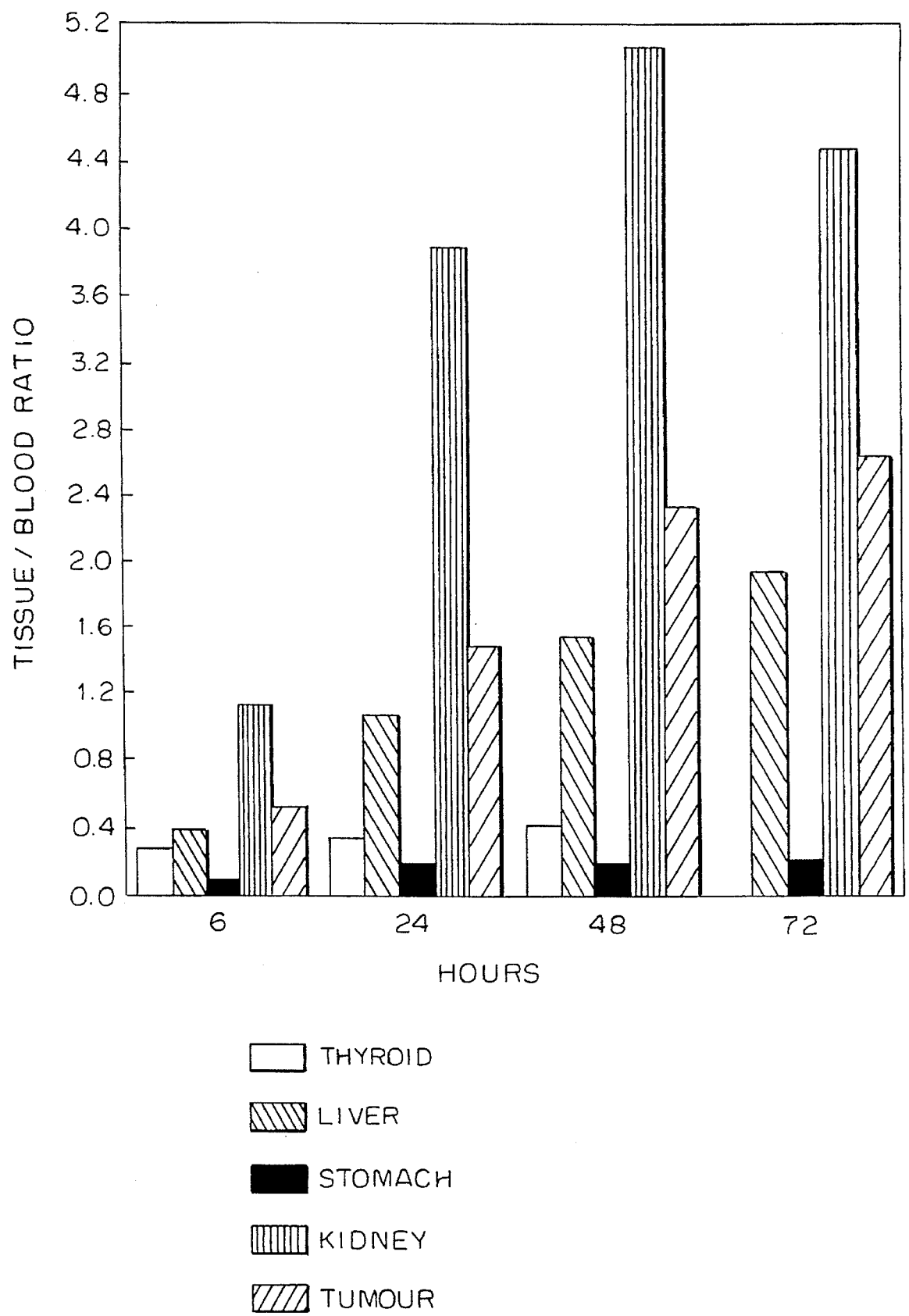
Figure 5C:
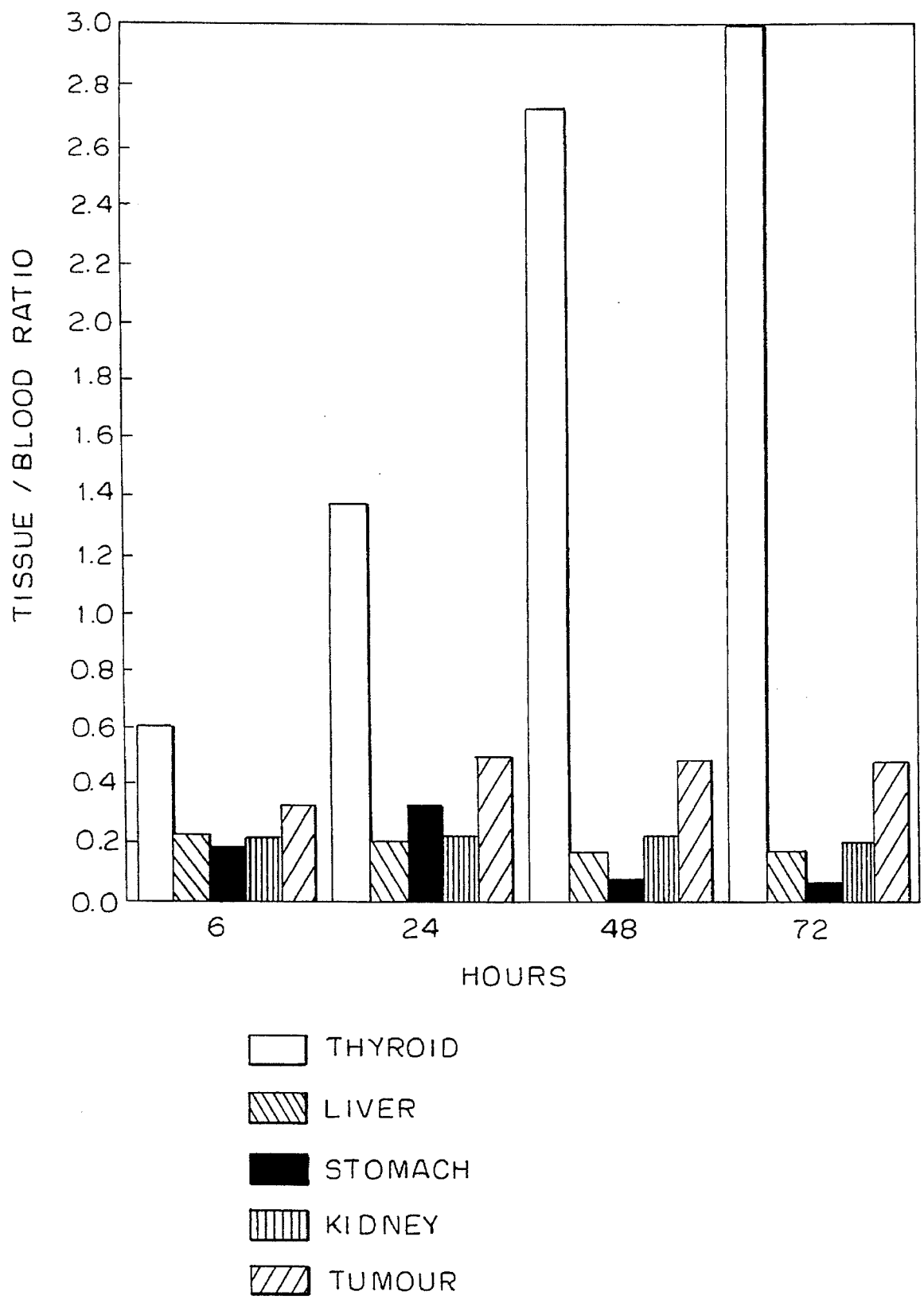

Using a triple label experiment, radioiodinated poly-H-IgG and radioiodinated MAb-155H.7 were compared to $^{111}$In-B-EDTA-MAb-155H.7. FIG. 5 summarizes the data for all three proteins in terms of the tissue to blood ratios for selected organs over the time period studied.

The blood clearance of the poly-H-IgG in the tumour bearing animals is similar to that obtained in the normal Balb/c mouse distribution. The activity remains elevated with a slow decline over the 72 hour study period. The radioiodinated MAb-155H.7 and $^{111}$In-chelated MAb-155H.7 differ distinctly in biodistribution. The iodinated MAb-155H.7 follows the same general pattern as the poly-H-IgG with blood activity being slightly lower. The $^{111}$In-B-EDTA-MAb-155H.7, however, shows rapid clearance from the blood with a steady decline over 72 hours.

Uptake of both $^{125}$I and $^{131}$I in thyroid and stomach indicate the metabolism of both the radioiodinated proteins. It should be noted that there is more of the $^{131}$I in both of these organs suggesting that MAb-155H.7 is metabolized more quickly than the poly-H-IgG preparation.

Liver activity of $^{111}$In is higher than either $^{131}$I or $^{125}$I. However, the $^{111}$In levels in the turnout bearing mice are not nearly as high as were seen in the normal Balb/c mice with the chelate labeled poly-H-IgG (6% of the injected dose per g of liver for $^{111}$In-B-EDTA-MAb-155H.7 as compared to 18% for $^{111}$In-B-EDTA- poly-H-IgG at 72 hours).

Liver uptake also differs with $^{131}$I-MAb-155H.7 being higher in the liver than $^{125}$I-poly-H-IgG.

The kidney shows a significant difference in the amount of $^{111}$In and $^{131}$I retained by this organ. Since PAB-EDTA-$^{111}$I is excreted quickly through the kidney, part of the high uptake seen here could be due to the excretion of metabolized chelate. Another possibility that could explain the high uptake in the kidney is active uptake of the MAb itself through specific receptors. Boniface et al. (Journal of Nuclear Medicine Vol. 27, page 688; Renal Tubular receptor Imaging with Iodine 131-Labeled Peanut Lectin: Pharmacokinetics and Renal Clearance Mechanism in Animals) have demonstrated the presence of a T-like structure in the kidney which binds lectin. The ratio of the kidney to blood ratio for $^{111}$In over the kidney to blood ratio for $^{131}$I is 7.22±0.93. The stability of this ratio over 72 hours points to the persistence of the MAb in the kidney and may be support for the active uptake of the MAb by the kidneys.

Bone uptake of $^{111}$In activity is low when compared to that seen in the normal mouse distribution and indicates the high stability of this chelate in vivo with regard to transchelation to transferrin.

Tumour uptake is virtually the same for the radioiodinated proteins but $^{111}$In accumulates over 72 hours. The lack of difference between radioiodinated poly-H-IgG and radioiodinated MAb-155H.7 was surprising. Although the MAb-155H.7 was not generated against the TA3/Ha tumour cell, it was hoped that some specific accumulation of the MAb would occur in vivo due to the presence of T-like epiglycanin on the tumor cell surfaces. This appears not to be the case with radioiodinated MAb-155H.7.

The accumulation of both radioiodinated proteins in the tumor could be due to non-specific processes or there may be radioiodinated antibodies in the poly-H-IgG preparation that may have some specificity for the TA3/Ha cells. Since this is a polyclonal preparation, it is possible that there may be a variety of antibodies present that could bind to the tumour cells.

Also, evidence is now appearing in the literature that suggests local metabolic processes in the tumor cells may be releasing radioiodine from radioiodinated proteins and returning it to the circulation whereas the catabolized $^{111}$In remains stored in the tumor cell. Pimm, et al., Eur. J. Nucl. Med., 11:300 (1985); Hagan, et al., J. Nucl. Med., 26:1418 (1985). This is supported by our studies where there is steady accumulation of the $^{111}$In over 72 hour and a stable or steady decrease of radioiodine levels in the tumor over 72 hours. Examining the percent dose remaining in each animal shows highest retention of $^{111}$In with the $^{125}$I from poly-H-IgG only slightly lower. Retention of $^{131}$I from MAb-155H.7 is very low and declines rapidly from 6 to 24 hours with a slow but steady decrease thereafter.

Thus, it is evident that the radioiodine label for MAb distribution is less stable than $^{111}$In. As well, a distinct difference is observed in the general distribution of the two radiolabels. The rapid blood clearance of $^{111}$In-labeled MAb enhances the tumor-to-blood ratio by reducing the blood background normally seen with radioiodinated MAbs. Poor tumor visualization with the radioiodinated MAb-155H.7 is likely related to lack of intact radioiodine-labeled MAb uptake rather than to a diminished accumulation of the MAb itself.

Summary Review of Eleven Patients Given 155H,7 Antibody and Scan Result

There have been 11 patients (8 F, 3M) treated to date. (See Table 19) Ten of the 11 patients had metastases and all of them had been previously treated (ten of them had received two of surgery, chemotherapy or radiotherapy). The ages ranged from 31 to 60.

Non-specific, transient reactions to the test dose (0.1) occurred in three patients. They were local, mildly inflammatory reactions which subsided within one hour and were not associated with any itch or discomfort. No reactions have resulted from the injection of MAb-115H7.

The first 5 patients (2 rectum, 1 each cecum, colon, and ovarian) were all given an antibody dose of 4 mgm with scans done at 48 hours. One patient also had a scan at 72 hours which confirmed the 48 hour result. There were 2 positive and 3 negative results with the side effects being minimal. One patient suffered from claustrophobia during scanning which is for him a chronic problem and another had a transient unilateral eyelid swelling of questionable significance.

Patients 6 through 10 were all breast cancer patients who had received treatment. At the 48 hour scan there were 3 negative and 2 positive reactions (one of these positives were confirmed at 72 hours). One patient had nausea and vomiting and one suffered ribcage pain.

The eleventh patient, using an antibody dose of 16 mgm, had a negative scan result of 48 hours with some general pain.

TABLE 19

| Patient Initials | Age | Sex | Primary Diagnosis | Metastases | Treatments | Test dose Reaction | Antibody Dose | 48 Hour Problems | 48 Hour Scan | 72 Hour Problems | 72 Hour Scan | Present Status |
|---|---|---|---|---|---|---|---|---|---|---|---|---|
| DB | 41 | M | cecum | low, colon | S, C | none | 4 mgm | nil | NEG | NOT DONE | | alive |
| MT | — | F | rectum | adrenal | S, C | none | 4 mgm | nil | NEG | NOT DONE | | alive |
| JM | 57 | M | rectum | liver | S, C | local | 4 mgm | claustrophobia | POS | NOT DONE | | deceased |
| KN | 31 | M | colon | lung, liver | S, C | none | 4 mgm | swollen eyelid | NEG | NONE | NEG | alive |
| LJ | 60 | F | ovarian | pulm, abdom | C, RT | none | 4 mgm | nil | POS | NOT DONE | | deceased |
| ML | 40 | F | breast | liver, bone | RT | none | 8 mgm | nil | NEG | NOT DONE | | alive |
| SL | 42 | F | breast | pleura | S, C | neg | 8 mgm | nausea, vomitting | POS | NOT DONE | | alive |
| SW | 53 | F | breast | supraclav, liver | S, C | local | 8 mgm | nil | NEG | NOT DONE | | alive |
| EW | 44 | F | breast | NIL | S, C | none | 8 mgm | nil | NEG | NOT DONE | | alive |
| MJ | 54 | F | breast | lung, liver | S, C | none | 8 mgm | ribcage, pain | POS | NONE | POS | alive |
| JS | 49 | F | breast | bone, liver, lung, pelvis | RT, C | local | 16 mgm | pain | NEG | NOT DONE | | alive |

NONE:
All "local" test dose reactions were non-specific inflammatory flares which were resolved in less than one hour.

Monoclonal Antibody Administration to Dogs

The dogs studied were canine cancer patients presented to the Western College of Veterinary Medicine at the University of Saskatchewan, Saskatoon. One dog had multiple mixed mammary tumors; three dogs, osteogenic sarcoma of the forelimb; and one dog, a fibrosarcoma occurring on the tibia.

Routine clinical analyses to evaluate hematopoietic, hepatic, pancreatic, and renal function were performed before administration of radiolabeled antibodies. Patients were tested for immediate hypersensitivity to the murine monoclonal by the intradermal injection of 100 ug of antibody in PBS. Thyroid uptake of $^{131}$I was blocked by daily oral administration of potassium iodide. The radiolabeled antibody was injected slowly in the cephalic vein through a 0.22u Milipore filter. In some patients unlabelled antibody was injected concurrently with the iodinated antibody (Table 20). Serial blood samples were collected at 5 minutes, 24 hours, 48 hours, 72 hours, and 96 hours following administration of the $^{131}$I antibody in the tumor patients.

In the normal dog blood samples were also collected at 5 minutes, 15 minutes, 30 minutes, 1 hour, 2 hours, 3 hours, 6 hours, 20 hours.

Tissue distribution of the injected antibody was evaluated by gamma camera scanning 24 hours, 48 hours, 72 hours and in some cases 120 hours after antibody injection in the tumor patients and at 3 hours, 24 hours, 72 hours, and 96 hours in the normal dog. All animals were imaged with a GE 400 A MaxiCamera interfaced with a MDS A$^3$ computer system. The images were acquired on a 64×64 matrix for a total of 200K.

Bloodpool subtraction was performed by the administration of autologous red blood cells labelled with 10mCl of $^{99m}$Tc using a modified Brookhaven method.

Following injection of radiolabeled monoclonal antibody for immunoimaging four animals with bone neoplasms were additionally administered 1–1.5 mgm/kgm unlabelled antibody. Tumor masses were subsequently surgically removed from these dogs 24 hours, eight days, fourteen days, and one month following injection of unlabelled antibody (Table 21).

The persistence of antibody 155H.7 in the blood of tumor bearing patients following the in vivo administration of milligram quantities of antibody was evaluated by immunohistochemistry. Serum samples obtained from the dogs were incubated undiluted on a 155H.7 known positive tumor tissue section followed by biotinylated antimurine IgG and ABC solution as previously described.

Impression smear samples and tissue sections of surgically excised tumors obtained from canine patients following in vivo administration of 155H.7 were stained directly for the presence of 155H.7 by the application of biotinylated anti-mouse IgG followed by the ABC complexes. Excised tumors were also examined for their ability to bind additional antibody in vitro by application of 1/1000 dilutions of antibody 155H.7.

Table 20 details the disappearance of the radiolabeled monoclonal antibody from the blood of the normal and tumor bearing dogs. The rates of disappearance of the antibody were similar in all dogs and were not substantially affected by the amounts of either radiolabeled or cold antibody administered to the dog or by the presence or size of an antibody binding tumor.

$^{131}$I labelled antibody 155H.7 was readily visible in tumor sites at 24, 48, 72, 96, or 120 hours following antibody injection. In advanced neoplasms there was also an increase in the vascularization within the tumor such that binding of the antibody was demonstrated most reliably following subtraction of the bloodpool. There was no evidence of localization of $^{131}$I labeled antibody 155H.7 in any other tissue or organ in the normal dog or tumor patients.

Murine antibody was directly demonstrable on the cell surfaces of tumors excised 24 hours, eight days, fourteen days, and 30 days, following in vivo administration of milligram quantities of antibody 155H.7. There was no evidence of cytoplasmic accumulation of the antibody in excised tumor tissue sections (not shown). Excised tumors were able to bind additional quantities of antibody as shown by increased staining of tumors following in vitro incubation with 155H.7.

In tumor bearing dogs administered antibody 155H.7 at doses of 1.0–1.5 mgm/kgm serum persistence of the monoclonal was shown by staining of a known 155H.7 positive tumor by the serum of patient for periods of 3 days to 10 days. The duration of detection of the antibody seemed to relate in part to the approximate tumor mass. (Table 21).

Monoclonal antibodies will be most useful for in vivo diagnostic and therapeutic administration if they bind to antigens expressed solely on tumor cell surfaces in a homogenous fashion and not on the cell surfaces of normal tissues. The ideal antibody for in vivo administration will recognize an antigen which is not spontaneously shed into the serum to avoid complexing of the injected antibody. In addition the injection of the antibody should not stimulate shedding of the tumor antigen or its modulation through internalization.

Antibody 155H.7 was demonstrable on the cell surfaces of canine tumor cells up to 30 days following the in vivo injection of 10–15 mg/kg unlabelled antibody. The ability of excised tumor cells to bind additional 155H.7 exposed to the cells in vitro suggests that the injection of antibody did not elicit loss of surface antigen expression. The absence of cytoplasmic marking of tissue sections stained directly for murine immunoglobulin also implies that antigen modulation and internalization were not occurring. Sears and coworkers have detected antibody on excised tumors in man following the in vivo administration of antibody for only one or two days post antibody therapy, however, in these individuals there is evidence that normal tissues were concurrently binding the antibody.

This study has shown that intact $^{131}$I labelled monoclonal antibody 155H.7 localizes rapidly to and persists at the sites of tumor cells without discernable localization to other tissues in either normal or cancer bearing dogs. Preferential accumulation of monoclonal antibodies in tumor sites has been documented in several other systems in which the antigen has similarly been demonstrable on normal tissues. The mechanisms which account for this have not been fully elaborated, in some instances preferential accumulation of antibody in tumors is attributable to quantatively greater expression of the antigen in tumor cells compared with normal cells, however, this has not been the case in all instances.

About 50% of the radionuclide was cleared from the blood after 24 hours (Table 20). Radionuclide clearance rate did not appear to be mollified by the presence of antibody binding tumors of greatly varying masses or by the concurrent administration of milligram quantities of unlabelled antibody. Tills finding was in contrast to the rate of disappearance of subsequently administered unlabelled antibody (Table 3). It should be noted, however, that in dog 3 in which there was rapid disappearance of the unlabelled antibody the tumor mass had experienced dramatic enlargement and developed extensive inflammation and necrosis following injection of the radiolabeled antibody and prior to the injection of the unlabelled antibody. Other authors have reported that the clearance of in vivo monoclonal antibody is unrelated to the presence or absence of an antibody binding tumor that the blood clearance is greatly accelerated in tumor bearing individuals or even decreased compared with the clearance in normal individuals.

The sensitivity limits for the detection of tumor cells by radiolabeled 155H.7 has not yet been determined. There were no known metastases in any of these patients, nor were metastases apparent by the described immunoimaging technique. In this study the smallest known lesion was approximately 1 cm. in diameter which is similar to the sensitivity limits described for tumor detection with other radiolabeled tumor reactive monoclonal antibodies. It is possible that sensitivity limits of radiolabeled 155H.7 can be increased by the use of antibody fragments, other radioisotopes, or by using mixtures of similar monoclonal antibodies. The latter may be particularly of interest in tumors other than sarcomas in which greater heterogeneity of monoclonal antibody binding is noted histochemically.

Monoclonal antibody 15511.7 is a versatile agent for tumor diagnosis and therapy in dogs recognizing many tumors regardless of their cell type or organ of origin. These studies show that antibody 155H.7 rapidly localize to and persists in neoplastic tissues 155H.7 can be efficiently radiolabeled without significant loss of immunoreactivity and will successfully detect tumors as small as 1–2 cm in diameter. Biopsy samples from tumors show the 155}I.7 monoclonal antibody or the tumor cell surface up to 30 days following in vivo antibody administration. Administration of doses of up to 1.5 mg/kg (40 mg total dose) were without evidence of adverse effects. Antibody 155H.7 may provide a therapeutic benefit in spontaneously occurring canine neoplasms.

TABLE 20

Canine Tumor Patient Immunoimaging: tumor types, amounts of radiolabeled antibody and unlabelled antibody injected for immunoimaging, % radiolabel remaining in the blood at 24, 48, 72 and 96 hours post injection.

| Dog | Tumor | $^{131}$I 155H.7 + Cold Antibody (ug.) | % Radiolabel Blood 24 | 48 | 72 | 96 |
|---|---|---|---|---|---|---|
| | | | (hours post injection) | | | |
| 1 | osteogenic sarcoma | 100 + none | 58 | 35 | 27 | 19 |
| 2 | mammary | 100 + none | 49 | 37 | 24 | 37 |
| 3 | osteogenic sarcoma | 200 + 750 | 53 | 33 | 28 | 15 |
| 4 | chondro-sarcoma | 100 + 1000 | 57 | ND | 25 | 17 |
| 5 | osteogenic | 200 + 3000 | 52 | 30 | 22 | 12 |
| 6 | normal | 100 + none | 50 | ND | 27 | 14 |

TABLE 21

Canine Tumor Patient In Vivo Administration of Unlabelled Antibody 155H.7 tumor types, amounts of injected unlabelled antibody, approximate tumor dimensions, duration of serum detection of injected antibody, and day of tumor removal following antibody administration.

| Dog | Tumor | Injected 155H.7 (mg/kgm) | (total mg) | Tumor Dimensions (cm. × cm. × cm.) | Detection of serum Antibody (days) | Tumor Removal (days) |
|---|---|---|---|---|---|---|
| 1 | osteogenic sarcoma | 1.0 | 40 | 10 × 10 × 8 | 10 | 30 |
| 3 | osteogenic sarcoma | 1.5 | 35 | 10 × 10 × 5 | 8 | 8 |
| 4 | fibrosarcoma | 1.0 | 7 | 2 × 2 × 2 | 6 | 14 |
| 5 | osteogenic sarcoma | 1.0 | 20 | 30 × 30 × 20 | 3 | 2 |

Toxicity Trial

The in vivo localization and potential toxicity of antibody 155H.7 was examined by the slow intravenous administration of 1 mg. and 12 mg. of antibody, respectively, to two normal 6 kgm dogs. Hematatologic, renal, hepatic, and pancreatic function were monitored before injection, 24 hours, 48 hours and 72 hours following antibody administration. Respiratory rate, heart rate, gum color and refill time were monitored before injection, repeatedly during injection and 1 hour, 2 hours, 6 hours, 12 hours, 24 hours, 48 hours and 72 hours after antibody injection. The dogs were euthanized by intravenous barbiturate and 1 cm. cubes of all major organs and tissues quick frozen in liquid nitrogen for immunohistochemical investigation of 155H.7 localization. Tissues were also placed in 10% buffered formalin for routine histological evaluation.

No acute toxic or inflammatory effects were demonstrable by clinical, hematological, serological, or histopathological examination following the administration of 1 or 12 mgm of antibody 155H.7 in two normal 6 kgm. dogs. Monoclonal antibody 155H.7 was not demonstrable by ABC immunohistochemistry in cryostat tissue sections of al major organs collected 72 hours after antibody injection. It will be evident to those working in the art that specific binding fragments of antibody 155H.7 may also be useful in carcinoma imaging.

Hybridoma cell line 155H.7R120, which secretes MAb 155H.7, was deposited with the American Type Culture Collection, 12301 Parklawn Drive, Rockville, Md. 20852, USA on Oct. 29, 1987 and was assigned accession number HB9577. Also, hybridoma cell line 170H.82 R1808, which secretes MAb 170H.82, was deposited with the same institution on Jul. 16, 1991 and was assigned accession number HB10825. They will be made available to the public in accordance with applicable U.S. law and the Budapest Treaty, but this should not be construed as conveying a license to make, use or sell subcultures so obtained.

We claim:

1. Monoclonal antibody 155H.7.

2. An imaging agent which comprises the monoclonal antibody of claim 1, said antibody having been tagged to render it detectable in a patient under imaging conditions.

3. The imaging agent of claim 2, wherein the agent is substantially cleared from the blood in 72 hours or less time after administration to a patient.

4. A monoclonal antibody which specifically binds at least some human lung, colon and breast carcinoma and which specifically binds to TF-beta-HSA, but not to Tn-HSA, wherein said monoclonal antibody specifically binds the epitope specifically bound by monoclonal antibody 1155H.7.

5. The antibody of claim 4, wherein the epitope comprises a TF-alpha or TF-beta disaccharide.

* * * * *